United States Patent [19]
Hasseberg et al.

[11] Patent Number: 6,140,536
[45] Date of Patent: *Oct. 31, 2000

[54] PROCESS FOR OBTAINING 2-HYDROXY-4-METHYLTHIOBUTYRIC ACID (MHA)

[75] Inventors: Hans Albrecht Hasseberg, Grundau; Hans Joachim Hasselbach; Klaus Huthmacher, both of Gelnhausen; Volker Hafner, Langenselbod; Harald Heinzel, Frankfurt; Barbara Jager, Freigericht, all of Germany

[73] Assignee: Degussa-Huls AG, Frankfurt, Germany

[*] Notice: This patent is subject to a terminal disclaimer.

[21] Appl. No.: 09/091,796
[22] PCT Filed: Dec. 5, 1996
[86] PCT No.: PCT/EP96/05437
   § 371 Date: Sep. 1, 1998
   § 102(e) Date: Sep. 1, 1998
[87] PCT Pub. No.: WO97/23452
   PCT Pub. Date: Jul. 3, 1997

[30] Foreign Application Priority Data

Dec. 23, 1995 [DE] Germany .................. 195 48 538

[51] Int. Cl.$^7$ .................................................. C07C 315/00
[52] U.S. Cl. ............................................................ 562/581
[58] Field of Search ...................... 562/526, 581

[56] References Cited

U.S. PATENT DOCUMENTS 5,847,207  12/1988  Suchsland et al. .................... 562/581

FOREIGN PATENT DOCUMENTS 0142488  5/1985  European Pat. Off. .

*Primary Examiner*—Elli Peselev
*Attorney, Agent, or Firm*—Pillsbury Madison & Sutro LLP

[57] ABSTRACT

A method for the isolation of 2-hydroxy-4-methylthiobutyric acid (MHA), wherein MHA is isolated from a reaction mixture obtained by addition of hydrogen cyanide (HCN) to methylmercaptopropionaldehyde (MMP) and hydrolysis by sulphuric acid of the methylmercaptopropionaldehyde cyanohydrin (MMP-CH) thus obtained. The reaction mixture is brought into contact in a liquid/liquid extraction system with an organic solvent substantially immiscible with water, in order to form an extraction solution which contains the solvent and the MHA transferred out of the reaction mixture. By bringing the salt content of the reaction mixture, prior to the liquid/liquid extraction, to a concentration of about >50 wt. % (wt./wt.), preferably >55 wt. %, referred to the sum of the inorganic constituents of the reaction mixture, the coordinated use of energy in the total system is improved, the evaporation of strongly corrosive solutions is avoided, the efficiency of the hydrolysis step is increased and the distribution coefficients during the extraction are improved. The MHA is isolated as the extract from this extraction solution by evaporation, and may be used as animal feed supplement.

18 Claims, 6 Drawing Sheets

Fig. 1: MHA isolation by salt separation and liquid/liquid phase separation in the MHA hydrolysate Fig. 2: MHA isolation by salt separation without liquid/liquid phase separation Fig. 3: MHA isolation without salt separation Fig. 4: MHA isolation by increasing the salt content

PROCESS FOR OBTAINING 2-HYDROXY-4-METHYLTHIOBUTYRIC ACID (MHA)

FIELD OF THE INVENTION

The invention relates to a method for the isolation of 2-hydroxy-4-methylthiobutyric acid (MHA), whereby MHA is isolated from a reaction mixture obtained by addition of hydrogen cyanide (HCN) to methylmercaptopropionaldehyde (MMP) and hydrolysis by sulphuric acid of the methylmercaptopropionaldehyde cyanohydrin (MMP-CH) thus obtained, the reaction mixture being brought into contact in a liquid/liquid extraction system with an organic solvent substantially immiscible with water, in order to form an extraction solution which contains the solvent and the MHA transferred out of the reaction mixture, and the MHA is isolated as the extract from this extraction solution by evaporation.

2-hydroxy-4-methylthiobutyric acid (MHA) is the hydroxy analogue of the essential amino acid methionine in racemic form and, like this acid, is an important additive in animal nutrition. In the rearing of poultry MHA exhibits growth-stimulating properties similar to those of the amino acids known for this. This additive is also becoming of increasing interest in other areas of animal nutrition.

MHA is mostly used in the form of aqueous concentrates containing, in addition to the monomer, a certain proportion of oligomers, mainly the dimeric and trimeric linear ester acids. The content of these oligomers is dependent on the conditions of preparation and on the concentration chosen. Owing to their lower nutritive efficiency and the unfavourable influence on the flow properties as a result of an increase in viscosity, it is however desirable to maintain their percentage as low as possible. Commercially available formulations having a total concentration of 88 to 90 wt. % contain up to 24 wt. %, corresponding to about 27 mol %, in total of oligomers, corresponding to a ratio of monomer to oligomers of about 3:1.

The general method for the preparation of MHA proceeds from 3-methylpropionaldehyde, also referred to as methylmercaptopropionaldehyde or MMP, which is reacted with hydrogen cyanide to form 2-hydroxy-4-methylthiobutyronitrile, also referred to as MMP cyanohydrin or MMP-CH (equation I).

(I)

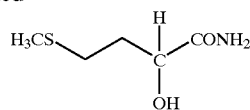

The MMP cyanohydrin formed is then hydrolysed, generally by strong mineral acids such as sulphuric acid or hydrochloric acid, via the intermediate step involving the formation of 2-hydroxy-4-methylthiobutyramide, also referred to as MHA amide (equation II)

(II)

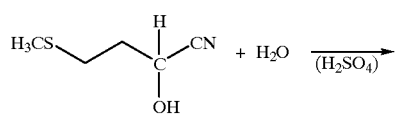

to prepare the methionine hydroxy analogue (MHA) (equation III).

(III)

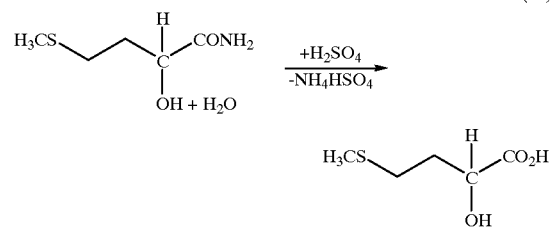

This hydrolysis may be carried out either in one step or in two steps. Here, by "steps" it is meant that mineral acid and/or water is added either once or twice in order to hydrolyse the MMP-CH, that is, the number of steps corresponds to the number of addition procedures.

BACKGROUND OF THE INVENTION

The following publications are cited as being close prior art:
EP-A-0 142 488=D1,
EP-A-0 143 100=D2,
EP-A-0 330 527=D3 and
WO-A-94/28717 = EP 93 924 374=D4.

A similar type of method for the isolation of MHA is known, for example, from D1. D1 employs two-step hydrolysis using sulphuric acid in order to isolate MHA in liquid form as a highly-concentrated aqueous solution.

According to D1, MHA is obtained after the hydrolysis reaction, which is carried out via the amide step using excess mineral acid under specified conditions of concentration and temperature, by means of a solvent extraction wherein use is made of certain solvents which are partially miscible with water.

According to the information in D1, the characterising feature of the method described in that document is to be seen in the isolation of MHA from the extraction solution, which is carried out in such a way that the isolation includes the removal of the organic solvent in the presence of at least about 5 wt. % of water, referred to the remaining extract (MHA). MHA is isolated from the extraction solution by distillation (see Examples), with steam distillation being preferred. As a result of removing the solvent from the extraction solution during the steam distillation, the discharge obtained is a mixture of MHA and water. The steam distillation is therefore carried out in such a way that the discharge contains at least 5 wt. % of water.

At another place in the text of D1 it is stated that the column conditions during the distillation are controlled in such a way that everywhere in the column, but at least in the bottom fraction, the liquid phase contains 5 wt. % of water.

It follows from this that in the absence of a sufficient quantity of water during the isolation of MHA from the extraction solution, the increasing formation possibly of undesirable by-products (dimers and oligomers) is to be expected.

Furthermore, in the distillation the steam serves as an operative agent for the complete removal of the extracting agent from the MHA solution, for example, through the formation of a low-boiling azeotropic mixture with the respective extracting agent.

Further embodiments of a method essentially similar in type are described in D2. In contrast to the preamble in D1, the hydrolysis of the MMP-CH by a mineral acid is described, with reference being made to the alternative possibility of using HCl instead of $H_2SO_4$. Altogether three additional variants are disclosed, which are concerned essentially with variations in the method of isolating MHA from the mineral acid hydrolysate or in the working up of the extract during the liquid/liquid extraction.

In an initial aspect according to D2, the hydrolysate is brought into contact with the organic solvent without previous separation of any essential fractions from solid substances contained therein. Moreover, according to D2 the conditions of the extraction are controlled so that the extract and the aqueous raffinate are the only liquid phases, which are formed during phase separation after the extraction.

A disadvantage of this first aspect is that the extraction is laden with the whole of the salt component formed in the hydrolysate during hydrolysis, which leads to a relatively high mass flow of hydrolysate and accordingly also of solvent. This results in correspondingly high energy costs in the solvent evaporation and condensation and costs of corresponding loss of solvent and of correspondingly large units for extraction and evaporation. A lowering of the operating and investment costs at this point in the process would therefore be desirable (especially in view of the size of such a plant and the potential for economy associated therewith).

The raffinate obtained from the extraction as a homogeneous liquid phase must, according to D1 or D2 or D4, be freed from remains of solvent by stripping or distillation, which is an undesirable additional expense.

In a second aspect, D2 refers to the separation of the organic solvent from the extract. On this point, it is stated that the separation is effected by subjecting the extract to a steam distillation, with the solvent being distilled off and a bottom fraction of aqueous MHA being formed.

A disadvantage of the use of steam is in particular the increased accumulation of aqueous solvent-laden steam condensate, which has subsequently to be freed from solvent at undesirable additional expense, such as that of distillation or stripping, in order then to return it to the process at a suitable point, or otherwise it has to be expensively disposed of, for example, by burning. Avoidance of additional stripping steam would therefore be desirable.

Finally, in a third aspect, D2 lays emphasis on the nature of the solvent to be used for the liquid/liquid extraction. The criteria to be considered in the selection of a suitable solvent include in particular the following points:

the boiling point of the solvent is to be between 60° C. and 200° C.;

the distribution coefficient for MHA in equilibrium between hydrolysate and solvent is to be at least approximately two;

the distribution coefficient of the solvent in equilibrium between extract and aqueous phase is to be at least approximately one;

the solubility of water in the solvent at room temperature is to be not more than about 12 wt. %.

The relatively high boiling point range, of from 60 to 200° C., of the solvents to be used here necessitates for the evaporation of the extract relatively elevated temperatures, which may impair the product, as well as additional auxiliaries, such as stripping steam, which is undesirable.

One of the considerable disadvantages of the methods in D1 and D2 consists however in the high salt content, which forms during the saponification and which nevertheless unfavourably contaminates the method for the isolation of MHA in an otherwise relatively elegant liquid/liquid extraction process. A working up of the inevitably resulting mixture of ammonium salts is in most cases not economic, the disposal is very hazardous from the environmental aspect and in the foreseeable future is likely to be prohibited by law even at sites having few rigid conditions.

There has been no lack of attempts to lessen or even to avoid the accumulation of salt from the saponification, but the advantages gained thereby were in every case achieved by accepting a number of other disadvantages or by dispensing with the elegant handling according to D1 and D2.

Thus in D3 there is disclosed a single-step method of hydrolysis using sulphuric acid as saponifying agent, which is carried out without solvent and leads directly to concentrated aqueous MHA solutions, with crystalline ammonium sulphate in marketable form being obtained as the coproduct. This object is achieved by neutralising the saponification mixture with ammonium hydroxide solution to the extent that the excess mineral acid and the ammonium bisulphate formed are converted into the neutral sulphate with the formation of two liquid phases, which for their part are separated and evaporated in order to isolate firstly liquid MHA and secondly crystalline ammonium sulphate. During this the different filtration and recirculation steps are combined in such a way that virtually no product is lost and no waste water contaminated with salt is formed. The resulting MHA is of a quality similar to that of the product obtained in D1.

However, even this relatively environmentally harmless method has various disadvantages. When reproducing this method, the Applicant of the present invention found that firstly, because of the comparatively high dilution of the sulphuric acid (20–50%), excesses of acid definitely higher than those given have to be used in order to achieve a complete cyanohydrin conversion. Moreover, to avoid precipitations of salt during neutralisation the method has to be carried out at higher dilution, to render possible a clean separation of the two liquid phases. Secondly, the ammonium sulphate isolated has a sticky consistency and is tainted with a strong smell, so that an aftertreatment such as, for example, a washing filtration or recrystallisation appears unavoidable and the method is thereby additionally made more expensive. Moreover the method—unlike what is postulated—consumes more energy in the evaporation steps than does the method cited by way of comparison in D1. Further, it is cost-intensive and very expensive as regards apparatus for the treatment of solids using filtration/centrifugation, which involves two separate paths, as well as the drying of the ammonium sulphate, which is not shown in the flow diagram.

A partial solution to the dilemma is promised by D4. D4 discloses the recovery of sulphuric acid from a sulphate-containing flow of waste material which arises during the preparation of 2-hydroxy-4-(methylthio)butyric acid by hydrolysis of 2-hydroxy-4-(methylthio)butyronitrile using sulphuric acid.

The recovery of sulphuric acid from ammonium sulphate, ammonium bisulphate and/or residues containing sulphuric acid has for a long time been prior art in the preparation of MMA and, just as is known for the residues from the saponification of acetone cyanohydrin, is achieved by combustion in a so-called split-contact plant of the flows of waste matter arising during saponification and extraction.

Here, in a manner familiar to the person skilled in the art, $SO_2$ is first of all produced as a decomposition product, which is oxidised on the contact catalyst to form $SO_3$, which is finally converted into sulphuric acid. The resulting sulphuric acid can then be returned again to the saponification process, while the other former constituents of the "load of salt" may be found substantially in the form of combustion gases.

Elegant as this method may be, it is also not free from disadvantages. Thus in the methods according to D1 and D2 flows of waste material arise, whereof the sulphate concentration is relatively low, but invariably too low to permit direct introduction into a split-contact plant. Hence a concentration or increase by mixing with concentrated flows of waste material from other processes is generally essential. Conventional solutions employed for the operation of split-contact plants have a sulphate salt content of >50 wt. %. Higher concentrations are even more preferred. Concentration by evaporation of the waste water arising from the isolation of MHA is however, owing to the high corrosiveness of the waste water, a relatively costly undertaking which, from the selection of special materials for the evaporation equipment to the special safety precautions required, is excessive and expensive.

SUMMARY OF THE INVENTION

In the light of the prior art cited and discussed here and of the disadvantages associated with the known methods, it is the object of this invention to provide another method for the preparation of 2-hydroxy-4-methylthiobutyric acid (MHA) of the type mentioned at the beginning, which is to be as simple and economical as possible as regards the working up of the reaction products and is to permit as highly concentrated a product as possible having as low as possible a content of dimers, oligomers and by-products. The new method is, if possible, to retain the advantages of the simple practicability of the step involving isolation of MHA in a liquid/liquid extraction, but is at the same time to permit as simple and rational as possible a disposal of the load of salt accumulating in the sulphate-containing waste water. In particular, a process is to be provided which inter alia permits the direct introduction of immediate flows of waste water into, for example, a split-contact plant, for the recovery of sulphuric acid which is usable and hence can be recirculated in the process.

This object and others not stated in detail are fulfilled by a method of the kind described at the beginning, which possesses the features of the characterising part of claim 1.

Advantageous variants of the method are placed under protection in the method claims dependent on claim 1.

By bringing the salt content of the reaction mixture, prior to the liquid/liquid extraction, to a concentration of about >50 wt. %, preferably >55 wt. % (wt./wt.), in each case referred to the sum of the inorganic constituents of the reaction mixture, according to the invention a method is provided which permits the preparation of MHA of outstanding quality and which at the same time in a not readily foreseeable manner solves, or at least surprisingly improves, the problem of the inevitably accumulating salt. In particular, there are furthermore a number of considerable advantages in increasing the salt concentration in a suitable manner after the hydrolysis but before the liquid/liquid extraction and hence never immediately prior to the possible connection to a split-contact plant.

The advantages mentioned include the following.

The evaporation otherwise appropriate prior to the introduction into a split-contact plant can be completely omitted.

More simply constructed and hence cheaper equipment is adequate for a concentration prior to the extraction because, owing to its particular composition, the concentrated solution is very much less aggressive at this particular point in the procedure and is therefore, in particular, also less corrosive.

In the case of at least partial shifting of the evaporation to a particular earlier point in the procedure there is an overall improved coordinated use of energy. Since already tempered (hot) hydrolysate is evaporated, and not raffinate which has already been cooled by extraction, the energy consumption is less.

In the course of a concentration by evaporation, the separation of unwanted low-boiling components of the hydrolysate is improved.

The hydrolysis of the MHA amide can be carried out in dilute solution, which results in a more complete chemical conversion. As it is better, in the hydrolysis of MHA amide using sulphuric acid, to employ a more dilute sulphuric acid (<40 wt. %) in order to allow the hydrolysis to take place as completely as possible, a less highly concentrated sulphuric acid can be used in the hydrolysis of the MHA amide, without its being necessary to anticipate that the subsequent extraction with an organic solvent will proceed less favourably. Owing to the concentration, a deterioration of the distribution coefficient is avoided and, in particular, less MHA remains in the raffinate during the extraction.

The method according to the invention therefore also fulfils in particular the requirement for an advantageous sulphuric acid concentration during the saponification and for the isolation of MHA from the hydrolysate in association with the provision of a raffinate which, owing to its composition, is more suitable for working up in a split-contact plant, while at the same time the energy balance overall is considerably improved.

The concentration of the salt in the hydrolysate of about >50 wt. % is a quite useable concentration for the subsequent working up by means of a split-contact plant. Ranges of from 55 to 60 wt. % are preferred. Particularly preferably the salt content of the reaction mixture is adjusted to about 60 to 80 wt. %, in each case referred to the sum of the inorganic constituents of the reaction mixture. To determine this value, which may also be termed the content referred to the "organic-free basis", essentially the water content, the sulphuric acid content and the content of sulphate ions and ammonium ions are used. These are the main inorganic constituents of the hydrolysate.

The term "concentration" includes, for the purpose of the invention generally, the increase in the salt concentration (referred to a basis free from organic constituents in wt. %="organic-free basis").

In a preferred variant of the method according to the invention, for the purpose of concentration a suitable quantity of ammonium sulphate is added to the reaction mixture (hydrolysate) which has formed as a result of the addition of HCN to MMP and hydrolysis by $H_2SO_4$ of the MMP-CH formed. The concentration of salt is accordingly increased by an addition. This variant in particular has a number of great advantages.

As already mentioned, in principle two mutually opposing effects have to be considered. On the one hand, the hydrolysis reaction should proceed as far as possible to completion, to which end a relatively lower amide concentration in the water present during the MHA amide saponification is appropriate. This inevitably results in a dilute solution of MHA and ammonium hydrogen sulphate. On the other hand, for the extraction process it is more advantageous to decrease the water content of the hydrolysate, that is, to have as high an MHA concentration as possible in the aqueous phase.

In D1 and D2 the hydrolysis is therefore carried out at an approximately <40 wt. % sulphuric acid concentration, which inevitably leads however to a dilute solution of MHA and ammonium hydrogen sulphate. To improve the subsequent extraction, in D1 and D2 the ammonium hydrogen sulphate is converted into neutral ammonium sulphate by the addition of anhydrous ammonia. This improves the corrosion behaviour of the solution but it can lead to the precipitation of solid substances, which may adversely affect the operation of an extraction. Accordingly, in D1 and D2 water may subsequently be readded, in order to bring the precipitated salts back into solution. In the course of this the concentration of MHA or salt should not however be lowered excessively, as otherwise extraction may be impeded.

In contrast to this, it is possible by the addition according to the invention of ammonium sulphate to carry out the hydrolysis of the MHA amide in more dilute solution, which results in a more complete conversion during the hydrolysis step. At the same time, the solution need not be neutralised. That is, the treatment with anhydrous ammonia and a possible redilution are unnecessary.

In a preferred embodiment, the method of the invention is carried out in such a way that, prior to isolation of MHA, ammonium sulphate is added in a quantity effective for salting out, with two phases being formed.

It is known from D1 and D2 that the presence of a high salt concentration (most advantageously ammonium hydrogen sulphate) "salts out" MHA and consequently has a favourable effect on the distribution coefficients. However, according to D1 and D2 a two-phase system is to be avoided, as this would interfere with the extraction. In contrast thereto, it has been found that a two-phase system formed by adding ammonium sulphate is particularly beneficial to the extraction step and altogether has a positive effect on this. Thus, for example, in one variant, solvent is added in such a quantity to a two-phase mixture obtained according to the invention, that two distinct phases are formed and a separation need be carried out only once.

Moreover, the addition of ammonium sulphate at this point of the method for isolating MHA has the general advantage of sparing the product. Through the addition of ammonium sulphate only the ammonium salt concentration is increased and not simultaneously the MHA concentration. An additional thermal stress (discoloration) of the target product aimed for need not occur; on the contrary, owing to the dissolving of the ammonium sulphate there is a lowering of the temperature. Nevertheless the distribution coefficient is favourably affected.

Although the variant of the ammonium sulphate addition discussed above possesses indisputable advantages in the sparing of the product, in an alternative variation of the method according to the invention it may be preferred to increase the salt concentration of the reaction mixture (hydrolysate) by evaporation.

Depending on the salt concentration in the raffinate, there may result increased discharge of solvent at the bottom of the column which, according to the publications D1, D2 or D4, has to be separated off in a raffinate stripping stage. In contrast to this, in the present invention it was ascertained that a solvent recovered in this way, due to a thermal stress in strongly acid medium is highly contaminated with by-products and is consequently unsuitable for direct recirculation into the extraction system.

Surprisingly, it has become apparent within the scope of the invention that even slight cooling of the product in the bottom of the column results in the discharge of a two-phase mixture of aqueous and organic raffinate, with the organic raffinate consisting to the extent of >97% of solvent, which immediately after a simple separation in a separating vessel can be passed back into the extraction system without further additional expense and the loss of solvent can in this way be minimised.

Consequently, a particularly preferred variant of the method according to the invention, wherein the salt concentration is increased by evaporation, is characterised in that at least three liquid phases immediately result from the extraction system.

Here in principle it is made possible for a homogeneous raffinate and an extract consisting of two liquid phases to be formed, the first liquid phase in the extract consisting substantially of MHA, solvent and small portions of water, while the second liquid phase consists substantially of water, MHA and small portions of salt, but it is far more advantageous that, in a variant of the method according to the invention, a homogeneous extract and a raffinate consisting of two liquid phases be formed. In this case, it is particularly advantageous that the first liquid phase in the raffinate consist substantially of ammonium salt and water and of small portions of MHA and organic solvent, while the second liquid phase consists substantially of organic solvent and of small portions of water and MHA.

In an advantageous variation of the method of the invention, the steps following the actual concentration by evaporation are conducted in such a way that the second liquid phase contains MHA in a quantity of from 0.01 to 0.5 wt. %, contains solvent in a quantity of from 90 to 99 wt. % and contains water in a quantity of from 0.1 to 10 wt. %, while the first liquid phase contains water in a quantity of from 20 to 50 wt. %, contains MHA in a quantity of from 0.01 to 0.5 wt. % and contains salt in a quantity of from 50 to 80 wt. %; the constituents of each phase taken separately must total 100 wt. %.

The extraction solution employed for the concentration by evaporation in order to isolate MHA is recovered from the reaction mixture by extraction. In principle, one may of course use all organic solvents known in prior art which exhibit a number of the properties already indicated above in the introduction to this description. The organic solvent employed for the extraction should be substantially immiscible with water. A partial miscibility of the organic solvent with water is however tolerable. The solvents which are suitable for the separation of substances in the liquid/liquid extraction include a large number which meet the conditions of chemical inertness and a low capacity to dissolve water. In general it is preferred that the solubility of water in the solvent at room temperature be not more than about 15 wt. %, preferably not more than 10 wt. %. Of the suitable solvents, those having a boiling point of between about 60° C. and about 200° C., preferably of between about 70° C. and 150° C., are preferred. The distribution coefficient between the solvent containing the extracted MHA, and the aqueous raffinate remaining behind after the contacting of the solvent and the MHA hydrolysate should be at least about 2 for MHA in equilibrium. This distribution coefficient is preferably at least 5. Moreover the distribution coefficient for MHA in equilibrium between extraction solution and washing water should be not less than about 1.0. In addition, the solvent is to exhibit a low toxicity.

A number of ketones, aldehydes and carboxylic esters are particularly suitable as solvents for the extraction. Particularly preferred solvents are ketones of relatively low molecular weight such as, for example, methyl n-propyl ketone, methyl ethyl ketone, methyl amyl ketone, methyl isoamyl ketone, methyl isobutyl ketone, ethyl butyl ketone and diisobutyl ketone. Aldehydes such as, for example, n-butyraldehyde, and esters such as, for example, ethyl acetate, n-butyl acetate, n-propyl acetate and isopropyl acetate are also suitable solvents for the extraction. Alcohols may also be used, although these are less preferred owing to their mutual solubility with water, a slow phase separation and the tendency to react with MHA.

Compared with these solvents already used or proposed in prior art, which are of course also of a certain usefulness for the present invention, totally unexpectedly it has been found that the use of ether compounds as solvents in the extraction is associated with many advantages. The ethers which may be used according to the invention include primarily those corresponding to the general formula I

$$R^1—O—R^2 \qquad (I),$$

wherein $R^1$ and $R^2$ independently of one another are identical or different $C_1$–$C_5$ alkyl, linear or branched. Suitable ether compounds include the following:

| No. | R1 | R2 | Bp [° C.] |
|---|---|---|---|
| 1 | Ethyl | Ethyl | 35 |
| 2 | n-Propyl | Methyl | |
| 3 | n-Propyl | Ethyl | |
| 4 | n-Propyl | n-Propyl | 90 |
| 5 | i-Propyl | i-Propyl | 69 |
| 6 | n-Butyl | Methyl | 71 |
| 7 | n-Butyl | Ethyl | 92 |
| 8 | n-Butyl | n-Propyl | |
| 9 | n-Butyl | n-Butyl | 143 |
| 10 | tert. Butyl | Methyl | 56 |
| 11 | tert. Butyl | Ethyl | 73 |
| 12 | tert. Butyl | n-Propyl | |
| 13 | tert. Butyl | n-Butyl | |
| 14 | Neopentyl | Methyl | |
| 15 | Neopentyl | Ethyl | |
| 16 | Neopentyl | n-Propyl | |
| 17 | Neopentyl | n-Butyl | |

The preferred ether compounds are firstly those which show no or only a low tendency to form peroxides such as, for example, MTBE. Asymmetrical ethers are also preferred.

Secondly, those compounds which have a boiling point of <60° C. are very useful, as they can be removed from the target product completely and easily.

Most especially preferred within the scope of the invention is the use of methyl tertiary butyl ether (MTBE), which meets all the above-mentioned criteria.

The actual extraction can in principle be carried out continuously or intermittently. An agitated tank, for example, is suitable for a batch-operated procedure. Preferably, however, the extraction is carried out in a continuous countercurrent extraction plant possessing an extraction zone designed for accelerating the mass transfer between solvent and aqueous phase. Thus it is advantageous, for example, to carry out the extraction in a cascade of continuous countercurrent mixer-settlers, a packed column, a perforated-plate column, preferably in the form of a pulsed column or column having moving plates, a rotary-disk extractor or a centrifugal extractor. In a particularly preferred embodiment, the extraction is carried out in a perforated-plate column for liquid/liquid extraction. Intermittent or pulsed flows, although cyclical and therefore not continuous for the purpose of rapid flow rates, are regarded as being "continuous" in connection with the present disclosure.

The extraction process is preferably controlled so as to set up and maintain the solvent phase as the continuous phase in the extraction zone.

The extract is if necessary washed with water in order to decrease to a minimum the salt content of the end product. Within certain concentration ranges of the resulting extract solutions the washing may however be dispensed with, in particular at sulphate contents of <0.5 wt. % and in view of the salt concentration of the raffinate flowing off, which should as far as possible not be further diluted. In a continuous countercurrent extraction system, the extract can be washed by being mixed with water at a point upstream, relative to the direction of the flow of organic substances, of the point at which the hydrolysate is introduced into the liquid/liquid extraction system. Thus, for example, in a vertical column and in the case of a solvent having a specific weight preferably of less than 1, solvents are introduced into the column at a point below the inlet point at which aqueous hydrolysate solution is introduced, and washing water is introduced into the column at a point above the inlet point of the hydrolysate solution.

The productivity of the extraction process is raised by operating at a somewhat elevated temperature, in order to provide for a relatively low viscosity of the solvent phase within the extraction system. Operation at a temperature within the range below the boiling point of the organic solvent used moreover has a barely favourable effect on the MHA distribution coefficients between the organic and the aqueous phase.

Within the scope of the invention, MHA can be isolated from the extraction solution by evaporation, as mentioned above. That is, the present invention is concerned with a further aspect, in particular with the evaporation of an extraction solution, such as is obtainable from a liquid/liquid extraction of a reaction mixture obtained, for example, by hydrolysis of MMP-CH using sulphuric acid. In this connection the evaporation is preferably carried out in such a way that the remaining extract contains less than 4 wt. %, preferably less than 2 wt. %, of water. Here, in a not readily foreseeable way, a highly concentrated liquid MHA containing particularly low proportions of oligomers and dimers is produced. In view of the known prior art, it is more than surprising that this can be achieved using a smaller proportion of water than may be inferred, for example, from the known publications (D1 and D2).

In a particularly preferred embodiment according to the invention, the organic solvent is removed during evaporation in a unit providing a brief residence time for the extraction solution in one evaporation step. The organic solvent is particularly preferably separated from the extraction solution during the evaporation by means, therefore, of a falling-film evaporator, film evaporator and/or short-path evaporator or with the aid of such a unit.

The expression "with the aid of such a unit" means, within the scope of the invention, that the aforesaid units providing a brief residence time for the extraction solution may also be combined with equipment, known to the person skilled in the art, for the separation of the solvent from extraction solutions. Here the units used for the combination need not necessarily be of the kind having a brief residence time. At this point one may mention, inter alia, distillation columns which may alternatively also be equipped for the introduction of steam or other suitable stripping agents. Combinations including several of the units mentioned having a brief residence time are also feasible.

In an advantageous variation of the method according to the invention, it is preferred that the evaporation of the extraction solution be carried out in such a way that as low a content of residual solvent as possible results. This is achieved, for example, by a combination of several of the above-mentioned units with a stripping stage, which may be contained as an additional unit or integrated into the above-mentioned units in the evaporator system, for example, by the direct introduction of the stripping medium into such an evaporator.

The specific conditions for the evaporation necessarily vary according to the particular solvent selected for use in the extraction. In principle, for the evaporation employing a separating unit providing a brief residence time for the extraction solution, it is preferred that the pressure during the evaporation be not more than 600 mbar, preferably not more than 400 mbar and particularly preferably not more than 200 mbar.

The temperature applied during the evaporation is as a rule likewise dependent on the solvent being separated. It is however intended, and therefore within the scope of the invention is also particularly preferred, that the temperature during the evaporation be not higher than 150° C. If this temperature is very definitely exceeded, there may be resulting thermal damage to the product aimed for. In this connection, the temperature during the evaporation is not necessarily to be understood as the contact temperature of the product with the surface of the evaporator unit equipped for brief contact with the product. The temperature during the evaporation means rather the average temperature in the evaporator unit. The temperature at the surface of the evaporator unit can in case of doubt be very much higher than 150° C. The brevity of the contact time in the evaporator units used is crucial. By this means a thermal damage is avoided, even if the contact temperature is definitely above 150° C.

Regarding the temperature distribution, within the scope of the invention it has been found that it is particularly advantageous to the product quality if the temperature of the remaining extract immediately at the discharge point from the evaporator unit be between 30 and 100° C., preferably from 50 to 95° C. and particularly preferably from 70 to 90° C.

As already mentioned, the residence time of the remaining extract is decisive for the quality and composition of the MHA product aimed for. In an advantageous development of the method according to the invention, the residence time of the remaining extract in the evaporation process is not longer than 1.5 h. This refers to the residence time in the entire evaporator system, which includes at least one evaporation step with a very brief residence time. The residence time in the unit having a very brief residence time, contrary to the maximum of 1.5 h given for the total residence time, is to be established rather in the range of minutes or less. In any rate, within the scope of the invention it is preferred, in the event that the evaporation consists solely of one film evaporator and/or falling-film evaporator and/or short-path evaporator, that the residence time in these units be not longer than 1 hour and preferably 40 min.

In a further aspect the method according to the invention, in addition to improving the isolation of MHA from the reaction mixture obtained by hydrolysis using sulphuric acid, also improves the hydrolysis of the actual MMP-CH. Thus in a preferred embodiment according to the invention, the hydrolysis of MMP-CH is carried out in such a way that, in a first step, MMP-CH is hydrolysed using from 60 to 85 wt. %, preferably from 65 to 80 wt. %, of sulphuric acid in the molar ratio of MMP-CH to $H_2SO_4$ of from 1.0:0.5 to 1:1.0, preferably from 1:0.6 to 1:0.95, at temperatures of from 30 to 90° C., preferably from 50 to 70° C., with substantially MHA amide being obtained. Here MHA amide is formed substantially from MMP cyanohydrin, the mixture formed being moreover substantially free from unreacted MMP cyanohydrin. In other words, this means that the hydrolysis proceeds virtually quantitatively.

A particularly advantageous target product can be isolated by the variations of the method for recovering MHA described in more detail above. The improved MHA is characterised according to the invention by containing more than 95 wt. % of total MHA as the sum of monomeric MHA, MHA dimers and MHA oligomers (=total MHA) and by having a water content of between more than 0.1 wt. % and less than 5 wt. %. In particular it has proved advantageous to the invention that, without greater losses of quality, an MHA can be obtained which is characterised in that it contains more than 98 wt. % of MHA as the sum of monomeric MHA, MHA dimers and MHA oligomers and has a water content of between 0.1 wt. % and less than 2 wt. % and a kinematic viscosity of >100 $m^2/s$ at 25° C. In this connection it has surprisingly been found that the kinematic viscosity, measured using a Cannon-Fenske viscometer, of high concentrate (that is, MHA having a content of active components of at least 98 wt. %), after storage and dilution is comparable with the kinematic viscosity of an 88 wt. % product. Notwithstanding a relatively high content of dimers and oligomers of about 50 wt. %, which is established in the high concentrate after storage for about 300 days at room temperature, when the stored high concentrate has been diluted with water to about 88 wt. % its kinematic viscosity corresponds to that of the 88 wt. % commercial product, which in parallel storage experiments had an equilibrium concentration of only about 25 wt. % of dimers and oligomers. The equilibrium state was achieved in both cases, both in the diluted high concentrate and in the commercial product. This fact is very surprising and proves to be a great advantage of a highly concentrated MHA variant prepared according to the invention. In view of the fact that dimeric and oligomeric constituents of MHA in general interfere in a manner disadvantageous to practical processing, it was all the more surprising that, in spite of high starting contents in the so-called high concentrate, an easily pumpable and therefore transportable mixture having a favourable viscosity can be obtained. This has various advantages: in particular the viscosity and above all the high content of active components result in the high concentrate being transportable more economically, as less water is transported; at the point of destination in the feed mill the high concentrate can still be diluted with water to the usual commercial concentrations, without unfavourable higher viscosities having to be accepted.

It has also been found within the scope of the invention that MHA of particularly high quality can be obtained by suitably conducting the hydrolysis reaction in combination with the mild evaporation and very brief residence time to be used according to the invention. This particularly advantageously obtainable MHA is characterised primarily by a content of the sum of dimers and oligomers, referred to the total sum of MHA, of <10 mol %, preferably of <7 mol %. This means that, contrary to the prejudice widely held in prior art, it is possible to obtain a highly concentrated MHA which, owing to an extremely low proportion of dimers and oligomers, is a very suitable form of short-term transport.

For a longer period of transport it is then preferred, by the addition of water and application of an elevated temperature, to reconvert into monomeric MHA the dimers and oligomers which increasingly form depending on the period of storage.

It is also possible within the scope of the invention to use the highly-concentrated MHA product for the preparation of animal feed supplements. Here it has been found that all nutritive useful materials basically required by the market can be prepared, without loss of quality, by mixing the MHA concentrate with water, methionine and/or salts of MHA (ammonium-MHA is preferred) (optionally $NH_3$ in order to produce $NH_4$-MHA).

First and foremost, in carrying out the invention it has been found that the mixtures are obtainable not only by addition of suitable components of the mixture such as water, methionine and/or ammonium-MHA from the outlet of the target MHA product from the evaporation step, but that likewise and moreover particularly advantageously in the case of mixing with ammonium-MHA, ammonia can be introduced directly into the MHA product from the evaporation. Here, depending on the quantity of ammonia added, a required proportion of MHA is converted into ammonium-MHA.

BRIEF DESCRIPTION OF THE DRAWINGS

The invention is further explained below with reference to the attached Figures. The following procedures are illustrated by the Figures.

DETAILED DESCRIPTION OF THE INVENTION

Figure 1:
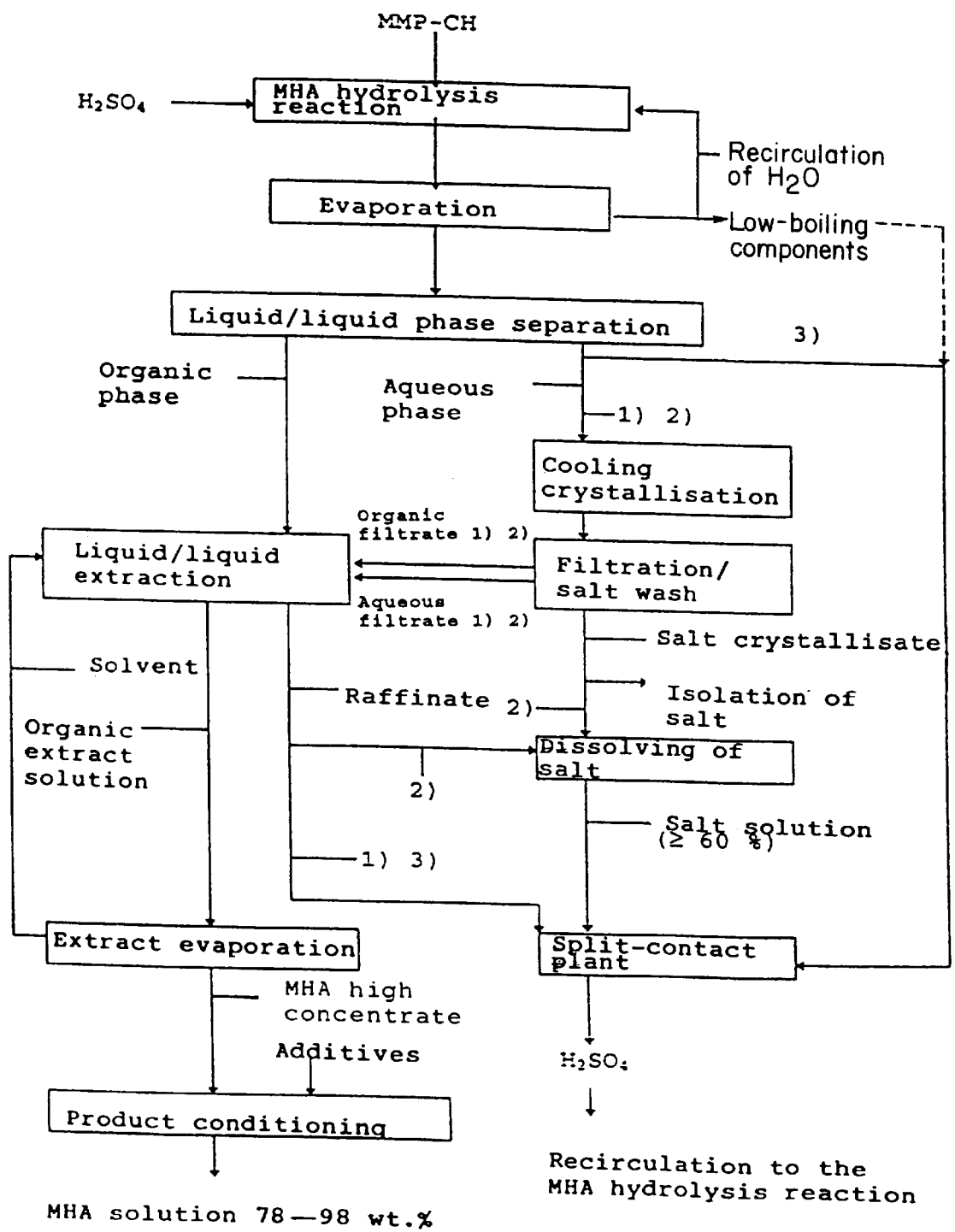
FIG. 1 shows a flow diagram for the isolation of MHA by salt separation and liquid/liquid phase separation in the MHA hydrolysate; the procedures 1), 2) and 3) can be followed independently of one another.

In a variant of the method shown in FIG. 1, MHP cyanohydrin (MMP-CH) is converted into the acid hydroxy analogue of methionine (MHA) in a two-step hydrolysis reaction using aqueous sulphuric acid. The primary MHA hydrolysate formed is then evaporated, starting from a concentration of <40 wt. % of MHA, to a concentration of >40 wt. %, preferably >45 wt. % of MHA, so that two liquid phases are formed.

The water obtained during the evaporation is condensed and returned to the hydrolysis step with the condensation temperature, in order to save energy, being maintained as close as possible to the temperature at which the hydrolysis takes place. The fraction of malodorous low-boiling components obtained is to a large extent separated by the steam, removed at the top, optionally with the aid of stripping gases, for example air, and is preferably passed without previous condensation directly to a combustion furnace. The latter may also be a component part of a plant for the recovery of sulphuric acid (a so-called split-contact plant).

The two liquid phases obtained from the bottom of the evaporation unit are separated from one another at a temperature which exceeds room temperature, but is at highest the temperature of the evaporation.

The lower aqueous phase, containing mainly the ammonium salt formed, is cooled until a considerable portion of the dissolved salts crystallises out. (Procedure 1) or 2)). The temperature required for this is below 30° C. The salt crystallisate obtained is separated from the supernatant solution by centrifugation or filtration. The salt crystallisate may be washed with a suitable organic solvent, or even with water or an aqueous salt solution, in order to remove useful material (MHA) still adhering.

The upper organic phase, containing mainly MHA as well as the aqueous filtrate and possibly the organic filtrate, is separated or, after partial or complete prior mixing, is together passed to a liquid/liquid extraction system (procedure 1) or 2)) and separated by means of an organic solvent into at least two phases, namely, into at least one mainly organic extract solution containing the solvent and MHA and small proportions of water and salt, and into an aqueous raffinate, which consists mainly of salt and water and which is then preferably passed to a plant for the recovery of sulphuric acid (procedure 1)), and optionally in addition into an organic raffinate, which consists mainly of solvent and small portions of MHA or water and which can be returned to the extraction system.

The organic extract solution is passed to a system for the evaporation of the extract, the evaporated solvent and possibly corresponding portions of water being recovered by condensation and returned to the extraction step. The MHA high concentrate obtained as discharge from the bottom of the evaporation unit is adjusted to the required MHA concentration, preferably between 78 and 98 wt. %, in a conditioning involving addition of required quantities of water and/or appropriate additives such as, for example, methionine or MHA-$NH_4$ salt.

The salt crystallisate, after an optionally performed salt wash, can be passed to a purifying or conditioning step (procedure 1)), wherein marketable ammonium sulphate is produced by the addition of appropriate quantities of $NH_3$ and subsequent crystallisation and drying, or else it can be passed in the form of the unrefined product directly to the drying unit. The salt crystallisate may also, in particular after being dissolved in water, be passed as a >60% concentrated solution to a plant for the recovery of sulphuric acid (procedure 2)). Here it is particularly advantageous to dissolve the salt crystallisate, still moist from filtration, in the raffinate from the extraction step and to pass the highly concentrated salt solution obtained, having a salt content of >75 wt. %, to the plant for the recovery of sulphuric acid, because a salt content of at least 60 wt. % is necessary for this and moreover each additional increase in concentration contributes to an improvement of the energy balance of such a plant. The concentration is possible here, especially in the absence of an energy-intensive evaporation of the salt solution obtainable from the process. All or part of the sulphuric acid thus recovered may be returned to the MHA hydrolysis step.

It can also be advantageous to pass the aqueous phase, without separation of salt, directly to a plant for the recovery of sulphuric acid, together with the raffinate from the extraction (procedure 3)). Here, too, it is advantageous that the salt content be definitely above 60 wt. %. A loss of about 2.5% of the theoretical yield of MHA occurs here, which is still dissolved in the aqueous phase. A considerable advantage here, however, is the great easing of the extraction or evaporation step, as the inlet flow to the extraction and hence also the use of solvent can be almost halved as compared with conventional methods (cf. D2), which is associated with an extreme saving in energy, especially as regards the evaporation and condensation of the solvent.

Figure 2:
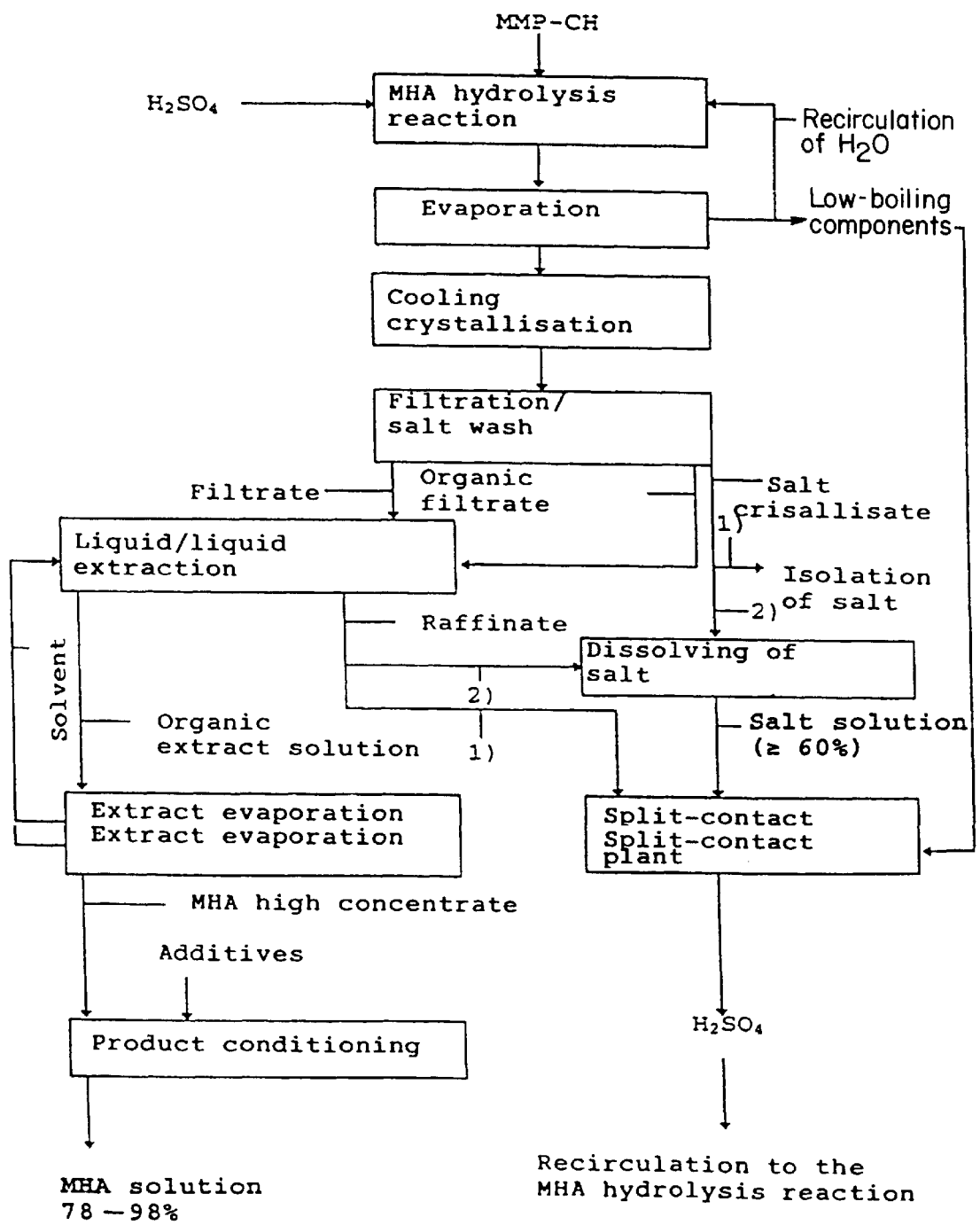
FIG. 2 likewise shows a flow diagram of an embodiment of the method according to the invention, wherein a salt separation without liquid/liquid phase separation is provided; here, too, the procedures 1) and 2) are independent of one another.

In a two-step hydrolysis reaction represented in FIG. 2, MMP cyanohydrin (MMP-CH) is converted into the acid hydroxy analogue of methionine (MHA), in a two-step hydrolysis reaction using aqueous sulphuric acid. The primary MHA hydrolysate formed is then evaporated, starting from a concentration of <40 wt. % of MHA, to a concentration of >40 wt. %, preferably >45 wt. % of MHA, so that two liquid phases are formed.

The water obtained during the evaporation is condensed and returned to the hydrolysis step with the condensation temperature, in order to save energy, being maintained as close as possible to the temperature at which the hydrolysis takes place. The fraction of malodorous low-boiling components obtained is to a large extent separated by the steam, removed at the top, optionally with the aid of stripping gases, for example air, and is preferably passed without previous condensation directly to a combustion furnace. The latter may also be a component part of a plant for the recovery of sulphuric acid.

The two liquid phases obtained from the bottom of the evaporation unit are cooled together with one another until a suspension of salt crystallisate and a homogeneous organic/aqueous liquid phase is formed. Here it is advantageous to cool the phases to room temperature.

The salt crystallisate is separated from the supernatant solution by centrifugation or filtration. The salt crystallisate is washed with a suitable organic solvent, or even with water or an aqueous salt solution, in order to remove useful material (MHA) still adhering.

The filtrate and possibly the organic filtrate are separated or, after partial or complete prior mixing, are together passed to a liquid/liquid extraction system and separated by means of an organic solvent into at least two phases, namely, into at least one mainly organic extract solution containing the solvent and MHA and small proportions of water and salt, and into an aqueous raffinate, which consists mainly of salt and water and which is then preferably passed to a plant for the recovery of sulphuric acid (procedure 1)).

The organic extract solution is passed to a system for the evaporation of the extract, the evaporated solvent and possibly corresponding portions of water being recovered by condensation and returned to the extraction step. The MHA high concentrate obtained as discharge from the bottom of the evaporation unit is adjusted to the required MHA concentration, preferably between 78 and 98 wt. %, in a conditioning involving addition of required quantities of water and/or appropriate additives such as, for example, methionine or MHA-NH$_4$ salt.

The salt crystallisate, after an optionally performed salt wash, can be passed to a purifying or conditioning step (procedure 1)), wherein marketable ammonium sulphate is produced by the addition of appropriate quantities of NH$_3$ and subsequent crystallisation and drying, or else it can be passed in the form of the unrefined product directly to the drying unit.

The salt crystallisate may also, in particular after being dissolved in water, be passed as a >60% concentrated solution to a plant for the recovery of sulphuric acid (procedure 2)). Here it is particularly advantageous to dissolve the salt crystallisate, still moist from filtration, in the raffinate from the extraction step and to pass the highly concentrated salt solution obtained, having a salt content of >75 wt. %, to the plant for the recovery of sulphuric acid, because a salt content of at least 60 wt. % is necessary for this and moreover each additional increase in concentration contributes to an improvement of the energy balance of such a plant. The concentration is possible here, especially in the absence of an energy-intensive evaporation of the salt solution obtainable from the process. All or part of the sulphuric acid thus recovered may be returned to the MHA hydrolysis step.

Figure 3:
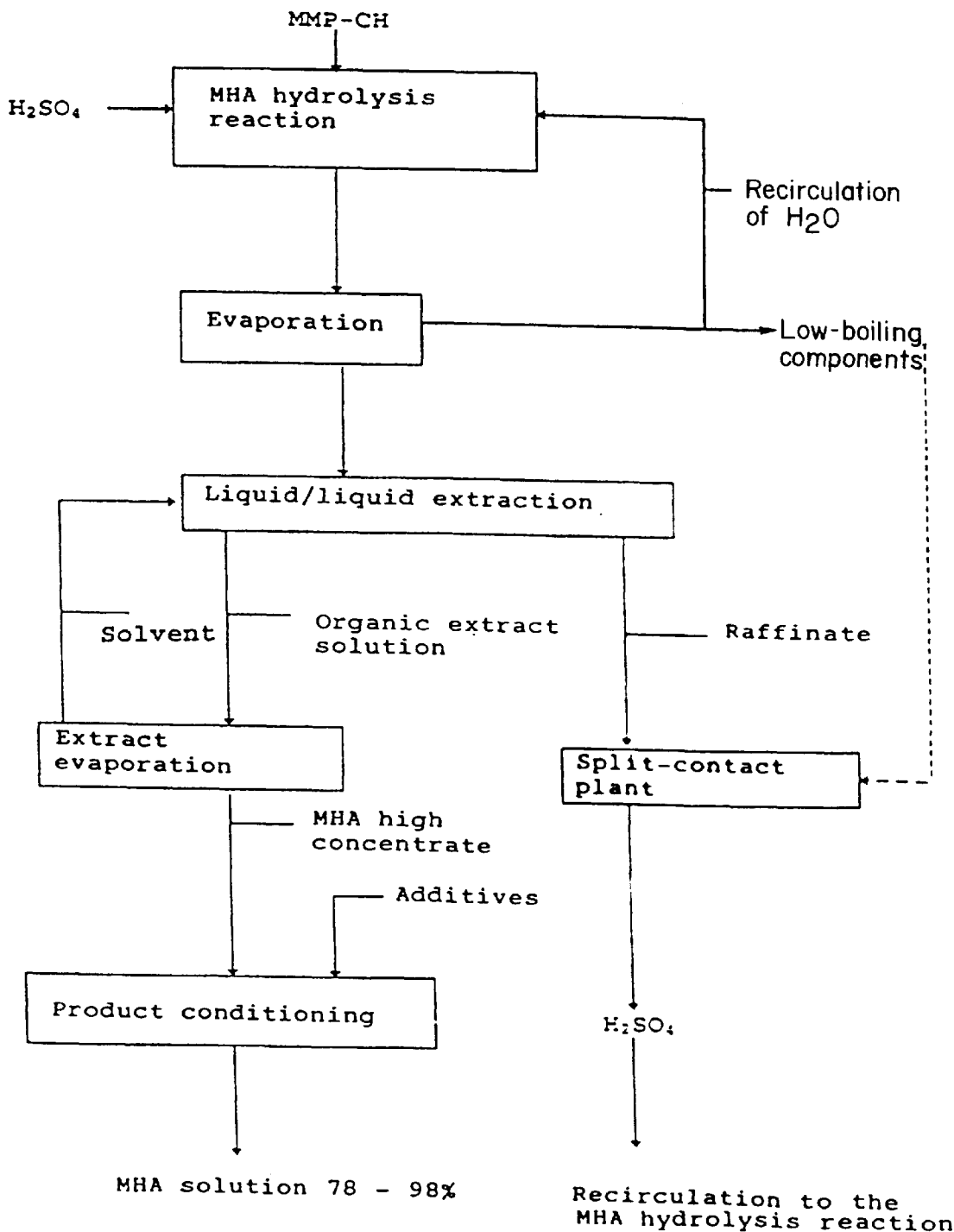
FIG. 3 shows a flow diagram of another embodiment according to the invention, whereby MHA is isolated without salt separation.

In the variant of the method represented in FIG. 3, MMP cyanohydrin (MMP-CH) is converted into the acid hydroxy analogue of methionine (MHA), in a two-step hydrolysis reaction using aqueous sulphuric acid. The primary MHA hydrolysate formed is then evaporated, starting from a concentration of <40 wt. % of MHA, to a concentration of >40 wt. %, preferably >45 wt. % of MHA, so that two liquid phases are formed.

The water obtained during the evaporation is condensed and returned to the hydrolysis step with the condensation temperature, in order to save energy, being maintained as close as possible to the temperature at which the hydrolysis takes place. The fraction of malodorous low-boiling components obtained is to a large extent separated by the steam, removed at the top, optionally with the aid of stripping gases, for example air, and is preferably passed without previous condensation directly to a combustion furnace. The latter may also be a component part of a plant for the recovery of sulphuric acid (a so-called split-contact plant).

The two liquid phases obtained from the bottom of the evaporation unit are if necessary cooled together, but only to the extent that no salt crystallisate is formed.

The product of the evaporation is passed to a liquid/liquid extraction system and separated by means of an organic solvent into at least two phases, namely, into at least one mainly organic extract solution containing the solvent and MHA and small proportions of water and salt, and into an aqueous raffinate, which consists mainly of salt and water and which is then preferably passed to a plant for the recovery of sulphuric acid. The required salt concentration of at least 60 wt. % depends absolutely essentially on the degree of evaporation of the primary hydrolysate. In this connection it should however be taken into account that this should be only so great that no salt crystallisates are formed within the extraction system as a result of an excessively high concentration. The salt concentrations achievable thereby are therefore less than those in the procedures shown respectively in FIGS. 1 and 2. All or part of the sulphuric acid thus recovered may be returned to the MHA hydrolysis step.

The organic extract solution is passed to a system for evaporating the extract, the evaporated solvent and possibly corresponding portions of water being recovered by condensation and returned to the extraction step. The MHA high concentrate obtained as discharge from the bottom of the evaporation unit is adjusted to the required MHA concentration, preferably between 78 and 98 wt. %, in a conditioning involving addition of required quantities of water and/or appropriate additives such as, for example, methionine or MHA-NH$_4$ salt.

Figure 4:
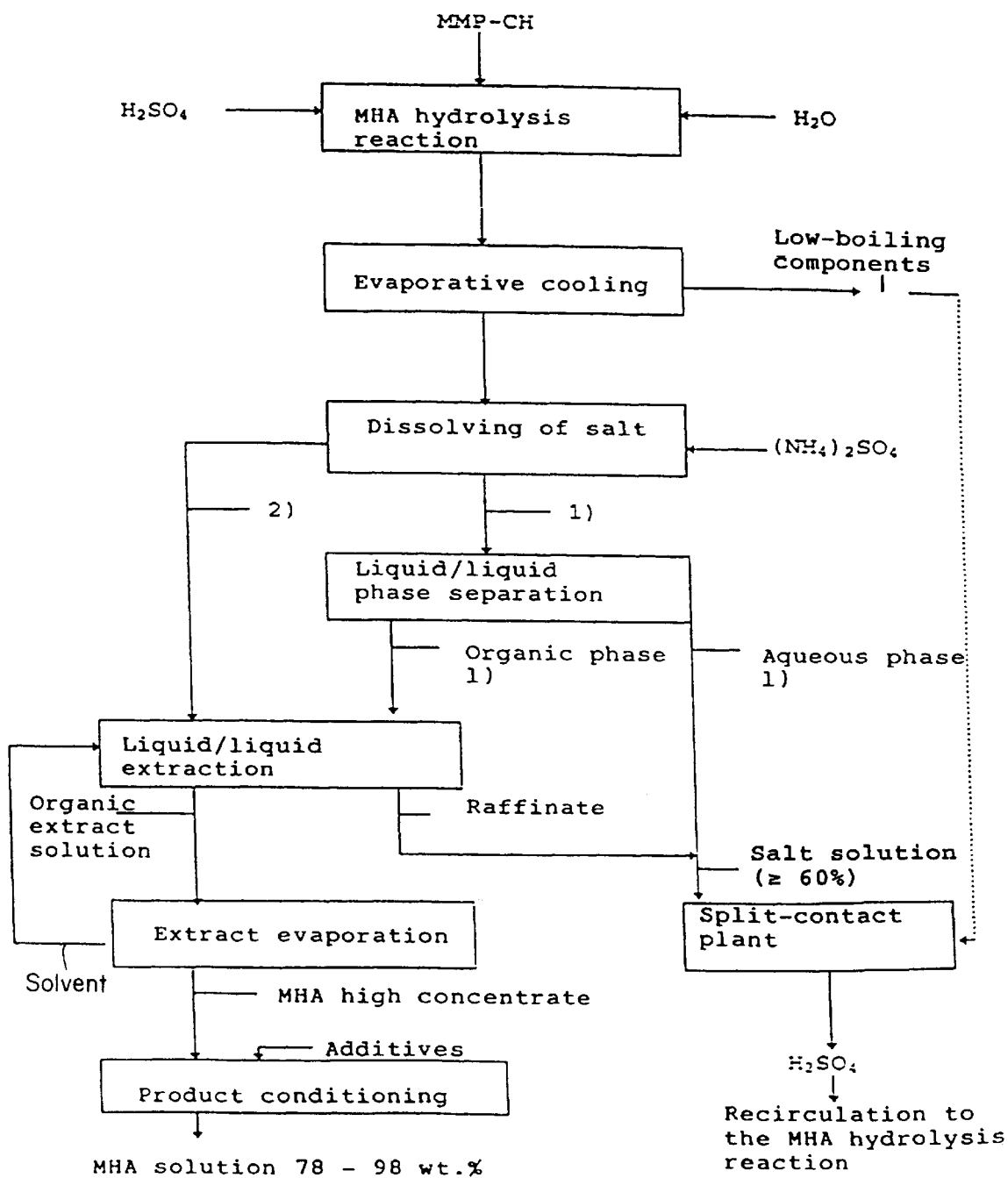
FIG. 4 shows a flow diagram of a further embodiment of the invention, whereby MHA is isolated after the salt content has been increased.

In the variation represented in FIG. 4, MHP cyanohydrin (MMP-CH) is converted into the acid hydroxy analogue of methionine (MHA) in a two-step hydrolysis reaction using aqueous sulphuric acid. The primary MHA hydrolysate formed, which has a concentration of <40 wt. % of MHA, is then subjected to evaporative cooling, wherein the temperature, starting from a reaction temperature of >100° C., is decreased to a suitable lower temperature, for example, 60° C. and at the same time a fraction of malodorous low-boiling components together with small quantities of steam is separated off by distillation, preferably with application of a vacuum and optionally with the aid of stripping gases, for example air, and can be passed without previous condensation directly to a combustion furnace. The latter may also be a component part of a plant for the recovery of sulphuric acid.

By the subsequent addition of $(NH_4)_2SO_4$ and/or $NH_4HSO_4$ to the homogeneous MHA hydrolysate solution, the salt concentration present therein is increased until two liquid phases are formed but at the same time a substantial proportion of undissolved solids is not left behind.

The two liquid phases are separated from one another at a temperature which exceeds room temperature (procedure 1)). The upper organic phase, containing mainly MHA, is passed to a liquid/liquid extraction system (procedure 1)) and separated by means of an organic solvent into at least two phases, namely, into at least one mainly organic extract solution containing the solvent and MHA and small proportions of water and salt, and into an aqueous raffinate, which consists mainly of salt and water.

The raffinate, preferably together with the lower, aqueous phase obtained from the liquid/liquid phase separation and containing mainly the ammonium salt formed, is passed to a plant for the recovery of sulphuric acid (procedure 1)). A loss of about 2.5% of the theoretical yield of MHA occurs here, which is still dissolved in the aqueous phase. A substantial advantage here is the great easing of the extraction or evaporation step, as the inlet flow to the extraction and hence also the use of solvent can be considerably decreased as compared with conventional methods (cf. D2), which is associated with an extreme saving in energy, especially as regards the evaporation and condensation of the solvent.

The organic extract solution is passed to a system for evaporating the extract, the evaporated solvent and optionally corresponding portions of water being recovered by condensation and returned to the extraction step. The MHA high concentrate obtained as discharge from the bottom of the evaporation unit is adjusted to the required MHA concentration, preferably between 78 and 98 wt. %, in a conditioning involving addition of required quantities of water and/or appropriate additives such as, for example, methionine or MHA-$NH_4$ salt.

Alternatively, the two liquid phases can also together be passed to a liquid/liquid extraction system (procedure 2)). The raffinate obtained, a >60% concentrated salt solution, can be passed directly to a plant for the recovery of sulphuric acid (procedure 2)), because a salt content of at least 60 wt. % is necessary for this and moreover each additional increase in concentration contributes to an improvement in the energy balance of such a plant. The concentration is possible here, especially in the absence of an energy-intensive evaporation of the salt solution obtainable from the process, which is a great advantage. All or part of the sulphuric acid thus recovered may be returned to the MHA hydrolysis step.

The following examples of preparation further explain the subject matter of the invention.

Analytical methods of determination and definitions

The contents of MMP cyanohydrin, MHA amide and MHA monomer respectively in the prepared solutions were determined quantitatively by means of HPLC by comparison with an external standard (pure substance).

The content of total MHA=MHA amide (optionally)+MHA(=total MHA) monomer+MHA (dimers+oligomers)

was determined by titrimetric determination of the thioether function using $KBr/KBrO_3$ standard solution and was expressed as the sum of the corresponding MHA monomer equivalents in [wt. %] or [g] or [mol] or [mol %].

The content of MHA dimers+MHA oligomers (DIM+OLI) was established by calculating the difference of total MHA less MHA monomer (+optionally MHA amide) and was expressed as the sum of the corresponding MHA monomer equivalents in [wt. %] or [g] or [mol] or [mol %].

The water content was determined by Karl-Fischer titration, the solvent content was determined by GC or by subtraction, the sulphate or ammonium content was found by ion chromatography using a standard method and the total salt content by converting the sulphate or ammonium contents or by subtraction.

EXAMPLE 1

Continuous Preparation of MHA Hydrolysate Solution

In a two-stage series of stirred-tank reactors 8.7 kg/h of an MHA amide solution was produced by a continuous charging of 4.2 kg/h (31.3 mol/h) of 97.7% MMP cyanohydrin and 4.5 kg/h (29.7 mol/h) of 65% aqueous $H_2SO_4$ at a temperature of 50° C. and with an average total residence time of 60 min. The MHA amide solution was further converted to form 12.3 kg/h of MHA hydrolysate solution by means of continuous dilution using 3.6 kg/h of water in a two-stage series of stirred-tank reactors with a reaction tube connected in tandem at a temperature of 90 to 110° C. and with an average total residence time of 180 min. The reaction solution accumulating initially was evaporated to small bulk by continuous introduction into an evaporator system at a pressure of 100 mbar and was cooled to a temperature of 50° C. at the discharge point. The pre-evaporated MHA hydrolysate obtained (10.8 kg/h) had the following analytical composition:

43.7 wt. % total MHA $\left. \begin{array}{l} 26.5 \text{ wt. \% } SO_4^{2-} \\ 5.2 \text{ wt. \% } NH_4^+ \\ 24.3 \text{ wt. \% } H_2O \end{array} \right\} \cong 32.0 \text{ wt. \% of salt}$

EXAMPLE 2

Preparation of MHA-MTBE Extract Solution

Experiment 1

2.5 kg of MHA hydrolysate (43.7 wt. % of total MHA, prepared as described in Example 1) together with 1.5 kg of MTBE (technical) were placed in a 5 l mixing vessel equipped with a bottom discharge valve and stirred intensively for 10 min at room temperature. After stirring had been concluded, the two liquid phases formed were separated from one another. The procedure was repeated in total 4 times, each time using fresh solutions.

The organic phases and the aqueous raffinate phases were each combined and analysed. The compositions of the phases in [wt. %] are shown in Table 1 below.

TABLE 1

|  | Organic phase (13.0 kg) [wt. %] |  | Raffinate phase (7.0 kg) [wt. %] |
|---|---|---|---|
| Total MHA | 41.8 |  | 1.9 |
| MHA | 38.4 |  | 1.9 |
| DIM + OLI | 3.4 |  | 0 |
| $H_2O$ | 4.8 | (calc.) | 40.0 |
| MTBE | (calc.) 53.0 |  | 0.04 |
| $SO_4^{2-}$ | 0.2 |  | 47.7 |
| $NH_4^+$ | 0.02 |  | 9.7 |

Experiment 2

Experiment 1 was repeated using 2.5 kg of MHA hydrolysate and 1.5 kg of MTBE, which had been recovered by evaporating MHA-MTBE extract solution (cf. Example 3). The compositions in [wt. %] may be seen in Table 2 below.

TABLE 2

|  | Organic phase (2.6 kg) [wt. %] |  | Raffinate phase (1.4 kg) [wt. %] |
|---|---|---|---|
| Total MHA | 42.0 |  | 1.9 |
| MHA | 37.7 |  | 1.9 |
| DIM + OLI | 4.3 |  | 0 |
| $H_2O$ | 4.8 | (calc.) | 40.0 |
| MTBE | (calc.) 53 |  | 0.04 |
| $SO_4^{2-}$ | 0.2 |  | 47.7 |
| $NH_4^+$ | 0.015 |  | 9.7 |

EXAMPLE 3

Preparation of MHA High Concentrate

Figure 5:
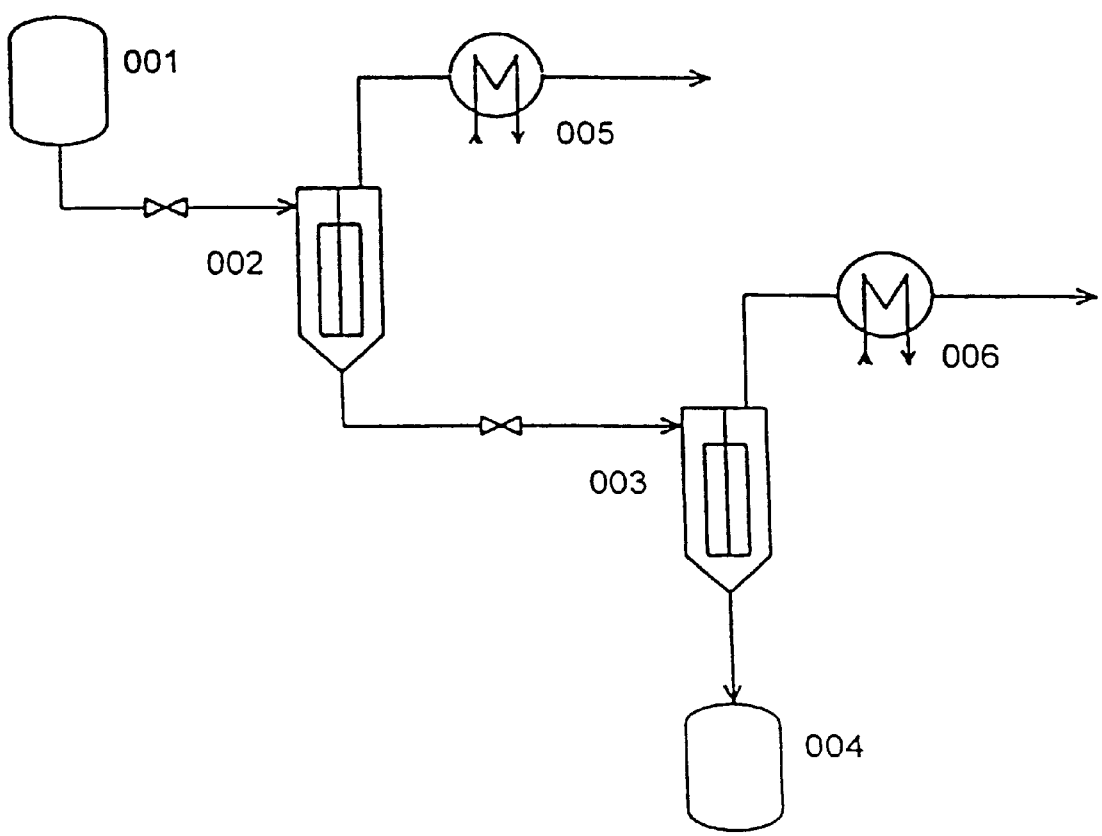
FIG. 5 shows a diagram of a suitable apparatus for carrying out the method of the invention.

In FIG. 5 is shown a diagram of the arrangement of the apparatus used for Example 3. This consists substantially of the following equipment:

| 001 | storage vessel |
|---|---|
| 002 | Sambay evaporators each having 0.06 m² exchange |
| 003 | surface and a heated double jacket |
| 004 | receiver for the MHA product |
| 005 | condensation system for distilled-off solvent |
| 006 | each consisting of a water-cooled and a brine-cooled laboratory cooler, a receiver and a water suction pump having an adjustable vacuum |

Description of the method with reference to FIG. 5

The MHA-MTBE extract solution leaving the extraction is fed continuously from the storage vessel 001 into the Sambay evaporator 002, which is heated externally. The discharge from 002 is fed via a needle valve into the likewise heated Sambay evaporator 003; the MHA product discharged therefrom is collected in the receiver 004 and there analysed. The distillate consisting of solvent is collected in the receivers of the two condensation systems 005 and 006 and from there can be returned to the extraction unit (cf. Example 2, Experiment 2).

Experiment 3

Use of 0.95 l/h (0.85 kg/h) of MHA-MTBE extract solution from Example 2, Experiment 1

Sambay 002:
pressure 250 mbar
temperatures:
  heating jacket 125° C.
  discharge point 79° C.
Composition of the MHA high concentrate in the bottom discharge from 002
Total MHA: 98.0 wt. %
$H_2O$: 0.5 wt. %
Sambay 003:
pressure 50 mbar
temperatures:
  heating jacket 140° C.
  discharge point 90° C.
  vapours 30° C.
Composition of the MHA high concentrate in the bottom discharge from 003
Total MHA: 99.0 wt. % MHA 83.9 mol % DIM+OLI 16.1 mol %
$H_2O$: 0.5 wt. %
MTBE: <10 ppm
0.36 kg/h of MHA high concentrate having the above composition was obtained from the bottom discharge of the Sambay evaporator 003.

Experiment 4

Use of 0.96 l/h (0.86 kg/h) of MHA-MTBE extract solution from Example 2, Experiment 2
Sambay 002:
pressure 250 mbar
temperatures:
  heating jacket 125° C.
  discharge point 96° C.
Composition of the MHA high concentrate in the bottom discharge from 002
Total MHA: 98.5 wt. %
$H_2O$: 0.9 wt. %
Sambay 003:
pressure 50 mbar
temperatures:
  heating jacket 120° C.
  discharge point 100° C.
  vapours 28° C.
Composition of the MHA high concentrate in the bottom discharge from 003
Total MHA: 100.0 wt. % MHA 85.7 mol % DIM+OLI 14.3 mol %
$H_2O$: 0.0 wt. %
MTBE: <1 ppm
0.36 kg/h of MHA high concentrate having the above composition was obtained from the bottom discharge of the Sambay evaporator 003.

EXAMPLE 4

Recovery of Salt from MHA Hydrolysate Prior to the Extraction by Liquid/Liquid and Liquid/Solid Phase Separation (cf. FIG. 1)

Experiment 5

MHA Separation by Liquid/Liquid Phase Separation and Liquid/Liquid Extraction Using MTBE 502 g of MHA hydrolysate containing 43.7 wt. % (219.4 g) of total MHA (prepared as described in Example 1) was evaporated at a pressure of 50 mbar to a content of 50 wt. % of total MHA. The concentrate (438.7 g) consisted of two liquid phases, which were separated from one another at T=65° C. The composition of the two phases is given in Table 3.

TABLE 3

|  | Organic phase (292.4 g) | Aqueous phase (143.4 g) |
| --- | --- | --- |
| Total MHA | 73.0 wt. %<br>≙ 213.4 g<br>≙ 97.3% of theor. | 3.9 wt. %<br>≙ 5.6 g<br>≙ 2.6% of theor. |
| H$_2$O | 10.6 wt. % ≙ 31.0 g | 20.6 wt. % ≙ 29.5 g |
| Salt (calc.) | 16.4 wt. % ≙ 48.0 g | 75.5 wt. % ≙ 108.3 g |

The aqueous phase was cooled to T=26° C. The salt crystallisate precipitated out, consisting of NH$_4$HSO$_4$+ (NH$_4$)$_2$SO$_4$, was filtered off. The composition obtained is given in Table 4.

TABLE 4

|  | Salt crystallisate (39.8 g) | Aqueous filtrate (103.6 g) |
| --- | --- | --- |
| Total MHA | 0.1 wt. % (calc.)<br>≙ 0.42 g<br>≙ 0.2% of theor. | 5.0 wt. %<br>≙ 5.18 g<br>≙ 2.4% of theor. |
| H$_2$O | 7.0 wt. % ≙ 2.8 g | 25.8 wt. % ≙ 26.7 g |
| Salt (calc.) | 92.9 wt. % ≙ 37.0 g | 69.2 wt. % ≙ 71.72 g |

The salt crystallisate was washed on the filter with 10 g of MTBE and the organic filtrate obtained (6.0 g) was analysed (4.8 g loss on evaporation of MTBE):

Total MHA=7.4 wt. %≙0.44 g≙0.2% of theoretical MHA loss via salt crystallisate: <0.2% of theoretical without salt wash and 0% of theoretical with salt wash The washed salt crystallisate was dried (35.8 g) and analysed:

SO$_4^{2-}$ 80.5 wt. %

NH$_4^+$ 18.5 wt. %

Salt 22.3% of theoretical

The organic phase (292.4 g), the aqueous filtrate (103.6 g) and the organic filtrate (6.0 g) were mixed with 232 g of MTBE and stirred intensively at room temperature for a brief period. After stirring had been concluded, the two liquid phases formed were separated from one another. The phases separated from one another had the compositions shown in Table 5.

TABLE 5

|  | Organic extract solution (475 g) | Raffinate (159 g) |
| --- | --- | --- |
| Total MHA | 46.0 wt. %<br>≙ 218.5 g (calc.)<br>≙ 98.4% of theor. | 1.8 wt. %<br>≙ 2.86 g<br>≙ 1.3% of theor. |
| H$_2$O | 3.5 wt. %<br>≙ 16.6 g | 25.3 wt. %<br>≙ 40.2 g |
| NH$_4^+$ | 0.034 wt. %<br>≙ 0.2 g | not observed |
| SO$_4^{2-}$ | 0.55 wt. %<br>≙2.6 g | not observed |
| Salt (calc.) |  | 72.9 wt. %<br>≙ 115.9 g |

The residual content of total MHA from the raffinate of the one-step extraction described here can be decreased to <0.1% of theoretical by subsequent extraction one or more times using fresh solvent, or by continuous extraction in a system comprising several theoretical plates.

The salt crystallisate (35.8 g) was dissolved in the raffinate (159 g) at 61° C. to form a clear solution. The salt solution thus obtained had the following composition:

Total MHA 1.4 wt. %≙1.3% of theoretical

H$_2$O 20.7 wt. %

Salt 77.9 wt. %

The solution thus obtained can with particular advantage be passed to a plant for the recovery of sulphuric acid, as its salt content is definitely more than 60 wt. %.

Experiment 6

MHA Separation by Liquid/Liquid Phase Separation and Liquid/Liquid Extraction Using MIBK 505 g of MHA hydrolysate containing 43.7 wt. % (220.7 g) of total MHA (prepared as described in Example 1) was evaporated at a pressure of 50 mbar to a content of 49.9 wt. % of total MHA. The concentrate (440 g) consisted of two liquid phases, which were separated from one another at T=60° C. The composition of the two phases is given in Table 6.

TABLE 6

|  | Organic phase (299 g) | Aqueous phase (141 g) |
| --- | --- | --- |
| Total MHA | 71.8 wt. %<br>≙ 214.7 g<br>≙ 97.3% of theor. | 4.0 wt. %<br>≙ 5.6 g<br>≙ 2.5% of theor. |

The aqueous phase was cooled to T=20° C. The salt crystallisate precipitated out, consisting of NH$_4$HSO$_4$+ (NH$_4$)$_2$SO$_4$, was filtered off. The composition obtained may be seen in Table 7.

TABLE 7

|  | Salt crystallisate (56 g) | Aqueous phase (83 g) |
| --- | --- | --- |
| Total MHA | 2.5 wt. % (calc.)<br>≙ 1.4 g<br>≙ 0.6% of theor. | 5.0 wt. %<br>≙ 4.15 g<br>≙ 1.9% of theor. |

The salt crystallisate was washed on the filter with 14 g of MIBK and the organic filtrate obtained (13.8 g) was analysed.

Total MHA=9 wt. % 1.2 g≙0.56% of theoretical MHA loss via salt crystallisate: <0.1% of theoretical The washed salt crystallisate was dried (40 g) and analysed:

SO$_4^{2-}$ 80.7 wt. %

NH$_4^+$ 18.8 wt. %

Salt 24.7% of theoretical

The organic phase (299 g), the aqueous filtrate (83 g) and the organic filtrate (13.8 g) were mixed with 250 g of MIBK and stirred intensively at room temperature for a brief period. After stirring had been concluded, the two liquid phases formed were separated from one another. These had the compositions shown in Table 8.

TABLE 8

|  | Organic extract solution (484 g) | Raffinate (144 g) |
|---|---|---|
| Total MHA | 217.1 g (calc.) = 98.4% of theor. | 2.05 wt. % ≙ 2.95 g ≙ 1.3% of theor. |

The residual content of total MHA from the raffinate of the one-step extraction described here can be decreased to <0.1% of theoretical by subsequent extraction one or more times using fresh solvent, or by continuous extraction in a system comprising several theoretical plates.

EXAMPLE 5

Recovery of Salt from MHA Hydrolysate Prior to the Extraction by Liquid/Solid Phase Extraction (cf. FIG. 2)

Experiment 7

MHA Separation Without Liquid/Liquid Phase Separation 505 g of MHA hydrolysate containing 43.7 wt. % (220.7 g) of total MHA (prepared as described in Example 1) was evaporated at a pressure of 50 mbar to a content of 49.9 wt. % of total MHA. The concentrate (440 g) was cooled to room temperature, with a suspension of salt crystallisate and a homogeneous liquid phase being obtained, which was separated by filtration. The composition found is shown in Table 9.

TABLE 9

|  | Filtrate (342.4 g) | Salt crystallisate (95.0 g) |
|---|---|---|
| Total MHA | 56.6 wt. % = 193.8 g ≙ 87.8% of theor. | 34.4 wt. % (calc.) ≙ 32.7 g ≙ 14.8% of theor. |

The salt crystallisate was washed on the filter with 20 g of MIBK and the organic filtrate (41.6 g) was analysed: Total MHA: 52.5 wt. %=21.8 g≙9.9% of theoretical.

The washed salt crystallisate was dried (52.8 g) and analysed:

Total MHA 6.1 wt. %=1.5% of theoretical $SO_4^{2-}$ 75.0 wt. %

$NH_4^+$ 18.4 wt. %

Salt 93.9 wt. %=30.7% of theoretical

The loss of MHA via the washed salt crystallisate was 1.5% of theoretical.

The filtrate (342.4 g) was taken up at room temperature in 244 g of MIBK and the organic filtrate (41.6 g) was added thereto, with an aqueous liquid phase separating. The two liquid phases were separated from one another and the composition found was that shown in Table 10.

TABLE 10

|  | Organic extract solution (480 g) | Raffinate (140 g) |
|---|---|---|
| Total MHA | 212.5 g (calc.) = 96.3% of theor. | 2.25 wt. % ≙ 3.15 g ≙ 1.4% of theor. |

The residual content of total MHA from the raffinate of the one-step extraction described here can be decreased to <0.1% of theoretical by subsequent extraction one or more times using fresh solvent, or by continuous extraction in a system comprising several theoretical plates.

The residual content of total MHA in the salt crystallisate can be further decreased by additional rewashing with solvent or water. A rewashing with water is preferably carried out using an aqueous solution of $NH_4HSO_4$ and/or $(NH_4)_2SO_4$, which is again preferably used several times and, at the latest on becoming completely concentrated, is returned to the extraction system for reextraction of the total MHA dissolved therein.

The MHA-containing organic filtrate can be returned to the solvent extraction system in order to isolate MHA from the organic filtrate and/or from the aqueous filtrate. At the same time a loss of MHA of about 0.5 to 12.5% of theoretical is advantageously avoided.

The salt crystallisates from Examples 4 and 5 are suitable for processing into marketable $(NH_4)_2SO_4$ by the addition of appropriate proportions of $NH_3$ and subsequent crystallisation. They may also be passed directly or, preferably, after being dissolved in water or in a suitable solution containing $NH_4HSO_4$ or $(NH_4)_2SO_4$ or both salts, to a plant for the recovery of $H_2SO_4$.

EXAMPLE 6

Liquid/Liquid Extraction of MHA Hydrolysate (cf. FIG. 3)

Experiment 8

Extraction Using MTBE 100 g of MHA hydrolysate containing 43.7 wt. % (43.7 g) of total MHA (prepared as described in Example 1) was mixed with 60 g of MTBE at room temperature and stirred intensively at room temperature for a brief period. After stirring had been concluded, the two liquid phases formed were separated from one another. The results are compiled in Table 11.

TABLE 11

|  | Organic extract solution (107 g) | Raffinate (52 g) |
|---|---|---|
| Total MHA | 39.9 wt. % (43.6 g) = 97.7% of theor. | 2.0 wt. % (1.0 g) = 2.3% of theor. |
| $H_2O$ | 4.16 wt. % | 38.7 wt. % |
| $NH_4^+$ | 0.02 wt. % | 9.6 wt. % |
| $SO_4^{2-}$ | 0.21 wt. % | 50.3 wt. % |

Experiment 9

Extraction Using MIBK 100 g of MHA hydrolysate containing 43.7 wt. % of total MHA was extracted using 60 g of MIBK in a manner similar to Experiment 8 (Table 12):

TABLE 12

|  | Organic extract solution (107.5 g) | Raffinate (51.5 g) |
| --- | --- | --- |
| Total MHA | 39.0 wt. % (41.9 g) = 95.9% of theor. | 2.4 wt. % (1.2 g) = 2.8% of theor. |
| $H_2O$ | 4.65 wt. % | 38.2 wt. % |
| $NH_4^+$ | 0.05 wt. % | 9.7 wt. % |
| $SO_4^{2-}$ | 0.38 wt. % | 50.4 wt. % |

A comparison of the two single-step solvent extractions shows that in the case of MTBE (Experiment 8) the organic extract solution takes up only half as much unwanted inorganic ammonium salt as in the case of MIBK (Experiment 9). Moreover even less MHA is lost via the raffinate phase when MTBE is used.

EXAMPLE 7

MHA Isolation After Increasing the Salt Content (cf. FIG. 4)

Experiment 10

MHA Separation by Liquid/Liquid Phase Separation and Liquid/Liquid Extraction 23 g of $(NH_4)_2SO_4$ in 598 g of MHA hydrolysate was dissolved in 43.7 wt. % (261.3 g) of total MHA (prepared as described in Example 1) at T=60° C. The solution (621 g) consisted of two liquid phases, which were separated at T=60° C. The following composition (Table 13) was found:

TABLE 13

|  | Organic phase (416 g) | Aqueous phase (205 g) |
| --- | --- | --- |
| Total MHA | 58.7 wt. % = 244.2 g = 93.4% of theor. | 7.8 wt. % = 16 g = 6.1% of theor. |
| $H_2O$ | 20.4 wt. % = 84.9 g | 32.7 wt. % = 67.0 g |
| Salt (calc.) | 20.9 wt. % = 86.9 g | 59.5 wt. % = 122.0 g |

The aqueous phase having a salt content of about 60 wt. % can be passed directly to a plant for the recovery of sulphuric acid.

The organic filtrate (416 g) was mixed with 250 g of MTBE and stirred intensively at room temperature for a brief period. After stirring had been concluded, the two liquid phases formed were separated from one another. Their composition is shown in Table 14.

TABLE 14

|  | Organic extract solution (522 g) | Raffinate (144 g) |
| --- | --- | --- |
| Total MHA | 47.5 wt. % = 248.0 g (calc.) = 94.9% of theor. | 2.4 wt. % = 3.4 g = 1.3 of theor. |
| $H_2O$ | 5.5 wt. % = 28.8 g | 39.0 wt. % = 56.2 g |
| $NH_4^+$ | 0.032 wt. % = 0.2 g | not observed |
| $SO_4^{2-}$ | 0.28 wt. % = 1.5 g | not observed |
| Salt (calc.) | — | 58.6 wt. % = 84.4 g |

The residual content of total MHA from the raffinate of the single-step extraction described here can be decreased to <0.1% of theoretical by subsequent extraction one or more times using fresh solvent, or by continuous extraction in a system comprising several theoretical plates.

The aqueous phase (205 g) and the raffinate (144 g) were combined. The salt solution thus produced (349 g) had the following composition:

Total MHA 5.6 wt. %

$H_2O$ 35.3 wt. %

Salt 59.1 wt. %

The approx. 60% salt solution can be passed directly to a plant for the recovery of sulphuric acid. A further concentration can be achieved by increased input of salt in the hydrolysate and by continuous extraction and complete separation of MHA from the raffinate.

Experiment 11

Separation of MHA by Liquid/Liquid Extraction

In a manner similar to Experiment 10, 23 g $(NH_4)_2SO_4$ was dissolved in 598 g of MHA hydrolysate. 372 g of MTBE was added to the resulting mixture comprising two liquid phases (620 g) and the whole was intensively stirred at T=40° C. After stirring had been concluded, the two liquid phases formed were separated from one another. The results are summarised in Table 15.

TABLE 15

|  | Organic extract solution (658 g) | Raffinate (332 g) |
| --- | --- | --- |
| Total MHA | 38.8 wt. % = 255.0 g (calc.) = 97.6% of theor. | 1.9 wt. % = 6.3 g = 2.4 of theor. |
| $H_2O$ | 4.4 wt. % = 30.0 g | 37.0 wt.% = 122.8 g |
| $NH_4^+$ | 0.012 wt.% = 0.08 g | not observed |
| $SO_4^{2-}$ | 0.15 wt. % 0.99 g | not observed |
| Salt (calc.) |  | 61.1 wt. % = 202.9 g |

The residual content of total MHA from the raffinate of the single-step extraction described here can be decreased to <0.1% of theoretical by subsequent extraction one or more times using fresh solvent, or by continuous extraction in a system comprising several theoretical plates.

The raffinate, having a salt content of >60 wt. %, can be passed directly to a plant for the recovery of sulphuric acid.

Washing of the organic extract solution with water can be dispensed with both in Experiment 10 and in Experiment 11, as the residual sulphate salt content is already extremely low. This is a great advantage, as in this way it is possible to avoid both additional operational expense and the undesirable dilution of the raffinate.

The organic extract solutions produced in Examples 4, 5, 6 and 7, similarly to those in Examples 2 and 8, can be continuously evaporated to the point of virtually complete removal of the solvent and to a water content of <5 wt. %. The MHA high concentrate thus produced can by appropriate conditioning be converted into various MHA product mixtures.

EXAMPLE 8

Figure 6:
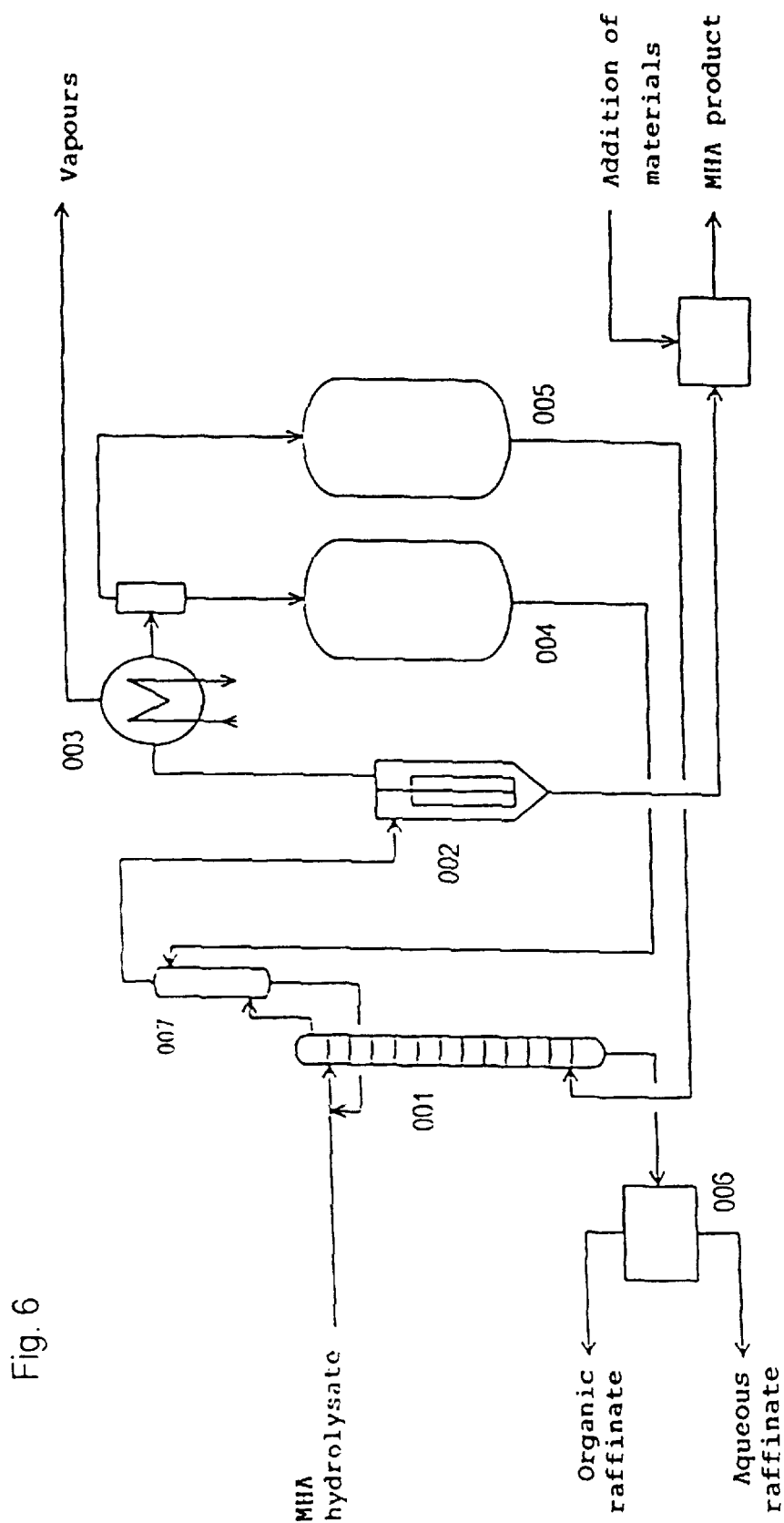
FIG. 6 shows a diagram of another suitable apparatus for carrying out the method of the invention.

Description of the Method with Reference to FIG. 6

A diagrammatic arrangement of the apparatus used for Example 8 is shown in FIG. 6. The reference numbers used indicate the following equipment, which substantially constitute the apparatus employed:

- (001) extraction column, for example, a pulsed perforated-plate column of 3 m in length, 2.1 cm internal diameter, having 60 perforated plates and a heated double jacket;
- (002) film evaporator, for example, a Sambay evaporator having 0.08 m$^2$ exchange surface and a heated double jacket;
- (003) condensation system, for example, a water-cooled glass condenser;
- (004/005) receiver for returned water or returned solvent
- (006) phase separator for organic and aqueous raffinate
- (007) washing zone for overflowing extract solution The MHA hydrolysate resulting from the MHA hydrolysis step, which consists substantially of MHA (monomer+dimers+oligomers+optionally amide), $(NH_4)_2SO_4$ and/or $NH_4HSO_4$ as well as water, after being preheated to the extraction temperature, is introduced into the extraction column 001 above the fortieth plate. The solvent (here methyl isobutyl ketone=MIBK) is likewise preheated and pumped into the bottom of the column (countercurrent principle). In addition the overflow from the column is subjected to washing water in a washing zone and the washing phase is returned to the inlet flow of hydrolysate. The aqueous raffinate containing substantially $(NH_4)_2SO_4$ and/or $NH_4HSO_4$ and water and the organic raffinate consisting mainly of solvent are withdrawn together at the bottom of the column, with cooling. The two phases are separated in a phase separator 006, the organic raffinate is returned to the extraction system and the aqueous raffinate is transferred out. The extraction solution containing substantially MHA, solvent and water is withdrawn at the head of the column and, after being passed through the washing zone 007, is then fed into the Sambay evaporator 002. There, under a vacuum and additional blowing in of $H_2O$ vapour as well as of a stream of $N_2$ shortly before the discharge from the evaporator, MIBK and $H_2O$ are together removed from the extraction solution. The evaporation was carried out in such a way that <2 wt. % of $H_2O$ was detectable in the discharge from the Sambay evaporator and the MHA high concentrate flowing out was virtually free from solvent.

The solvent/water mixture issuing from the evaporator 002 was first of all condensed in 003 and passed into a separating vessel in order to be separated. Water and solvent were each collected in a receiver 004 and 005 respectively and from there were returned to the extraction system. The discharge from the Sambay evaporator was cooled to room temperature and passed to a receiver intended for the product.

The composition of the extraction solution was analysed immediately after its leaving the washing zone 007 and the composition of the aqueous and of the organic raffinate solution respectively was analysed in each case immediately after their leaving the phase separator 006.

The composition of the MHA high concentrate was determined in the discharge from the bottom of the Sambay evaporator immediately after the outlet point.

The MHA hydrolysate solution used for the extraction was prepared from 114.7 kg (874 mol) of MMP cyanohydrin and 131.9 kg (874 mol, 1.00 mol equiv.) of 65% $H_2SO_4$ in a pressure-resistant 400 l agitated tank at a temperature of 50° C. and with a residence time of 60 min, followed by dilution with 96.7 kg of $H_2O$ and further reaction at a temperature of 90° C. and with a residence time of 120 min. The crude hydrolysate solution, after conclusion of the reaction, was freed from volatile by-products present by the application of a vacuum and subsequently analysed. The composition thus obtained of the MHA hydrolysate used for the extraction is given in Example 8, Experiment 12.

The conditions and results of Experiment 12 are summarised in tabular form below.

Experiment 12

Use of MHA Hydrolysate Obtained from MMP Cyanohydrin and 1.0 Mol Equiv. of $H_2SO_4$ Use in extraction:
Flow rates:
MIBK 6.7 kg/h
MHA hydrolysate 12.3 kg/h
total MHA 4.9 kg/h
washing $H_2O$ 1.3 kg/h
MIBK hydrolysate 0.55 [–]
Composition of MHA hydrolysate:
total MHA 39.5 wt. %
MHA 94.7 mol %
DIM+OLI: 5.3 mol %
$H_2O$: 28.7 wt. %
$SO_4^{2-}$: 27.5 wt. %
$(NH_4HSO_4)$: 33.2 wt. %
Extraction (001):
Temperature: 60° C. (average)
Compositions
of the extraction solution:
   MIBK 44.7 wt. % (calc.)
   total MHA 41.8 wt. %
   $H_2O$ 13.5 wt. %
of the aqueous raffinate:
   MIBK 77.5 ppm
   total MHA 0.1 wt. %
of the organic raffinate:
   MIBK 97.5 wt. % (flow rate 0.017 kg/h)
Evaporation 002
Pressure 600 mbar
Sambay
temperature
   in the heating jacket 180° C.
   at the top 85° C.

at the bottom not observed
stripping steam 0.5 kg/h
stripping gas $N_2$ 100 l/h
Composition of the MHA high concentrate in the discharge from the bottom of the column:
total MHA 98 wt. %
MHA 86 mol %
DIM+OLI: 14 mol %
$H_2O$: 2 wt. %
MIBK 40 ppm Approx. 4.9 kg/h of MHA high concentrate having the above composition was obtained from the discharge from the bottom of the Sambay evaporator. The organic raffinate was returned to the extraction column. The aqueous raffinate was transferred out for disposal directly and without further aftertreatment.

It was thus possible to avoid an additional distillation or stripping step for the removal of residual solvent from the discharge from the bottom of the column. The organic raffinate, which was withdrawn from the extraction column under mild conditions as the third liquid phase, could moreover be directly returned to the column without further purification.

This application claims priority from German application 195 48 538 6, filed Dec. 23, 1995, and is the National Phase of PCT/EP96/05437, filed Dec. 5, 1996, the entire disclosures of which are incorporated herein by reference.

What is claimed is:

1. A method for the isolation of 2-hydroxy-4-methylthiobutyric acid (MHA), comprising:
    adding hydrogen cyanide (HCN) to methylmercaptopropionaldehyde (MMP); and
    hydrolysing the thus formed methylmercaptopropionaldehyde cyanohydrin (MMP-CH) by,
        (a) in a first hydrolysing step, adding sulphuric acid thereto, thereby forming a reaction mixture containing substantially 2-hydroxy-4-methylthiobutyroamide (MHA-amide) and;
        (b) in a second hydrolysing step, adding water to the MHA-amide thus formed, thereby forming a reaction mixture containing substantially 2-hydroxy-4-methylthiobutyric acid (MHA);
    bringing the MHA containing reaction mixture into contact in a liquid/liquid extraction system with an organic solvent substantially immiscible with water, thereby forming an extraction solution which contains the solvent and the MHA transferred out of the reaction mixture, and
    isolating the MHA as the extract from this extraction solution by evaporation,
    with the proviso that in the first hydrolysing step (a), MMP-CH is hydrolyzed using from 60 to 85% sulphuric acid in the molar ratio of MMP-CH to $H_2SO_4$ of from 1.0:0.5 to 1:1.0 at a temperature of from 30 to 90° C., and
    in the second hydrolysing step (b) the MHA amide is hydrolyzed by the addition of water without further addition of $H_2SO_4$, at a temperature of up to 140° C., and
    an initial salt content of the reaction mixture, prior to the liquid/liquid extraction, is brought to a concentration of about >50 wt. % (wt./wt.), with reference to the sum of the inorganic constituents of the reaction mixture.

2. The method according to claim 1, wherein the initial salt content is adjusted by adding ammonium sulphate to the reaction mixture prior to liquid/liquid extraction.

3. The method according to claim 2, comprising:
    prior to isolation of the MHA, adding ammonium sulphate in a quantity effective for salting out.

4. The method according to claim 1, further comprising:
    increasing the salt concentration by evaporation.

5. The method according to claim 1, wherein:
    at least three liquid phases result from the extraction system.

6. The method according to claim 5, comprising forming:
    a homogeneous extract and a raffinate having first and second liquid phases.

7. The method according to claim 6, wherein:
    the first liquid phase in the raffinate consists substantially of ammonium salt and water and of small portions of MHA and organic solvent, and the second liquid phase consists substantially of organic solvent and of small portions of water and MHA.

8. The method according to claim 7, wherein:
    the first liquid phase contains water in a quantity of from 20 to 50 wt. %, MHA in a quantity of from 0.01 to 0.5 wt. % and salt in a quantity of from 50 to 80 wt. %, and the second liquid phase contains MHA in a quantity of from 0.01 to 0.5 wt. %,
    solvent in a quantity of from 90 to 99.9 wt. %, and
    water in a quantity of from 0.1 to 10 wt. %,
    the constituents of each phase taken separately totalling 100 wt. %.

9. The method according to claim 1, wherein:
    hydrolysis is carried out in the molar ration of MMP-CH to $H_2SO_4$ of from 1:0.6 to 1:0.95.

10. The method according to claim 1, wherein the organic solvent used to form the extraction solvent comprises one or more ethers.

11. The method according to claim 10, wherein:
    the solvent comprises an asymmetrical ether.

12. The method according to claim 11, wherein:
    the solvent comprises an ether having a boiling point of <60° C.

13. The method according to claim 10, wherein:
    the solvent comprises methyl tertiary butyl ether (MTBE).

14. The method according to claim 1, comprising:
    evaporating the extraction solution to a water content of <4%, and
    distilling off residual solvent from resulting concentrate.

15. The method according to claim 14, wherein the step of distilling off the residual solvent comprises stripping using steam.

16. The method according to claim 14 or claim 15, wherein,
    after removal of the solvent a product having a water content of <4% is obtained.

17. The method according to claim 16, wherein,
    the product has a water content of <3%.

18. The method according to claim 1, wherein the salt content of the reaction mixture is brought to a concentration of >55 wt. % (wt./wt.).

* * * * *